US011587195B2

(12) United States Patent
Calhoon et al.

(10) Patent No.: US 11,587,195 B2
(45) Date of Patent: Feb. 21, 2023

(54) IMAGE PROCESSING METHODS AND ARRANGEMENTS USEFUL IN AUTOMATED STORE SHELF INSPECTIONS

(71) Applicant: Digimarc Corporation, Beaverton, OR (US)

(72) Inventors: Sean Calhoon, Lake Oswego, OR (US); Tony F. Rodriguez, Portland, OR (US); Joel R. Meyer, Lake Oswego, OR (US); William Y. Conwell, Portland, OR (US)

(73) Assignee: Digimarc Corporation, Beaverton, OR (US)

( * ) Notice: Subject to any disclaimer, the term of this patent is extended or adjusted under 35 U.S.C. 154(b) by 325 days.

(21) Appl. No.: 16/752,337

(22) Filed: Jan. 24, 2020

(65) Prior Publication Data

US 2020/0234394 A1 Jul. 23, 2020

Related U.S. Application Data

(63) Continuation of application No. 15/830,874, filed on Dec. 4, 2017, now Pat. No. 10,552,933, which is a (Continued)

(51) Int. Cl.
*G06T 1/00* (2006.01)
*G06Q 10/087* (2023.01)
(Continued)

(52) U.S. Cl.
CPC ......... *G06T 1/0092* (2013.01); *G06Q 10/087* (2013.01); *A61B 17/00234* (2013.01);
(Continued)

(58) Field of Classification Search
CPC ..... G06T 1/0092; G06T 1/0007; G06T 1/005; G06T 2201/0065; G06T 1/0064;
(Continued)

(56) References Cited

U.S. PATENT DOCUMENTS

| 5,382,779 A | 1/1995 | Gupta |
| 6,122,403 A | 9/2000 | Rhoads |

(Continued)

FOREIGN PATENT DOCUMENTS

WO 2016051183 4/2016

OTHER PUBLICATIONS

Sawers, Bossa Nova's Retail Robots Ensure Store Shelves are Always Stocked, Venturebeat, Apr. 26, 2016.
(Continued)

*Primary Examiner* — Behrang Badii
(74) *Attorney, Agent, or Firm* — Digimarc Corporation

(57) ABSTRACT

Imagery captured by an autonomous robot is analyzed to discern digital watermark patterns. In some embodiments, identical but geometrically-inconsistent digital watermark patterns are discerned in an image frame, to aid in distinguishing multiple depicted instances of a particular item. In other embodiments, actions of the robot are controlled or altered in accordance with image processing performed by the robot on a digital watermark pattern. The technology is particularly described in the context of retail stores in which the watermark patterns are encoded, e.g., on product packaging, shelving, and shelf labels. A great variety of other features and arrangements are also detailed.

25 Claims, 10 Drawing Sheets

Related U.S. Application Data continuation-in-part of application No. 15/152,365, filed on May 11, 2016, now Pat. No. 10,007,964.

(60) Provisional application No. 62/429,564, filed on Dec. 2, 2016, provisional application No. 62/181,131, filed on Jun. 17, 2015, provisional application No. 62/164,490, filed on May 20, 2015.

(51) Int. Cl.

| | | |
|---|---|---|
| G06K 7/14 | (2006.01) | |
| A61B 17/00 | (2006.01) | |
| G06N 3/049 | (2023.01) | |
| G06K 7/10 | (2006.01) | |
| G06Q 20/20 | (2012.01) | |
| G05D 1/00 | (2006.01) | |
| G06Q 30/00 | (2023.01) | |
| G06V 10/10 | (2022.01) | |

(52) U.S. Cl.
CPC ....... G05D 1/0088 (2013.01); G06K 7/10861 (2013.01); G06K 7/1417 (2013.01); G06K 7/1421 (2013.01); G06N 3/049 (2013.01); G06Q 20/208 (2013.01); G06Q 30/00 (2013.01); G06T 1/005 (2013.01); G06T 1/0007 (2013.01); G06T 2201/0065 (2013.01); G06V 10/10 (2022.01)

(58) Field of Classification Search
CPC ...... G06T 3/40; G06Q 10/087; G06Q 20/208; G06Q 30/00; A61B 17/00234; G05D 1/0088; G06K 7/10861; G06K 7/1417; G06K 7/1421; G06N 3/049; G06N 3/0454; G06V 10/10; G06V 20/68; G06V 10/50; G06V 20/10; G06V 20/52
See application file for complete search history.

(56) References Cited

U.S. PATENT DOCUMENTS

| | | |
|---|---|---|
| 6,307,949 B1 | 10/2001 | Rhoads |
| 6,345,104 B1 | 2/2002 | Rhoads |
| 6,590,996 B1 | 7/2003 | Reed |
| 6,912,295 B2 | 6/2005 | Reed |
| 6,973,197 B2 | 12/2005 | Miller |
| 6,975,744 B2 | 12/2005 | Sharma |
| 7,231,061 B2 | 6/2007 | Bradley |
| 7,340,076 B2 | 3/2008 | Stach |
| 8,189,855 B2 | 5/2012 | Opalach |
| 8,210,430 B1 | 7/2012 | Grant |
| 8,380,349 B1* | 2/2013 | Hickman ............... H04L 67/303 701/25 |
| 8,401,224 B2 | 3/2013 | Rhoads |
| 8,429,004 B2 | 4/2013 | Hamilton |
| 8,447,863 B1* | 5/2013 | Francis, Jr. ......... G06F 16/2468 709/227 |
| 8,508,527 B2 | 8/2013 | Jeong |
| 8,630,924 B2 | 1/2014 | Groenevelt |
| 9,015,072 B2 | 4/2015 | Wu |
| 9,076,042 B2 | 7/2015 | Saptharishi |
| 9,097,800 B1 | 8/2015 | Zhu |
| 9,245,160 B2 | 1/2016 | Graube |
| 9,317,775 B2 | 4/2016 | Moraleda |
| 9,330,474 B1 | 5/2016 | Shekar |
| 9,373,057 B1 | 6/2016 | Erhan |
| 9,984,451 B2 | 5/2018 | Gormish |
| 10,007,964 B1 | 6/2018 | Calhoon |
| 10,176,452 B2* | 1/2019 | Rizzolo ............... G01C 21/206 |
| 10,285,765 B2 | 5/2019 | Sachs |
| 2002/0114491 A1 | 8/2002 | Sharma |
| 2002/0147597 A1 | 10/2002 | Connors |
| 2006/0100967 A1 | 5/2006 | Grimaldi |
| 2006/0104598 A1 | 5/2006 | Gilles |
| 2008/0077511 A1* | 3/2008 | Zimmerman ........ G06Q 10/087 705/28 |
| 2009/0059270 A1 | 3/2009 | Opalach |
| 2009/0060259 A1 | 3/2009 | Goncalves |
| 2009/0094140 A1 | 4/2009 | Kwan |
| 2009/0192921 A1 | 7/2009 | Hicks |
| 2009/0282025 A1 | 11/2009 | Winter |
| 2010/0065634 A1 | 3/2010 | Nakamura |
| 2010/0123005 A1 | 5/2010 | Guess |
| 2010/0150434 A1 | 6/2010 | Reed |
| 2010/0287057 A1 | 11/2010 | Aihara |
| 2011/0214044 A1 | 9/2011 | Davis |
| 2011/0303748 A1 | 12/2011 | Lemma |
| 2012/0046071 A1 | 2/2012 | Brandis |
| 2012/0078989 A1 | 3/2012 | Sharma |
| 2012/0208592 A1 | 8/2012 | Davis |
| 2012/0214515 A1 | 8/2012 | Davis |
| 2012/0323620 A1 | 12/2012 | Hofman |
| 2013/0182114 A1 | 7/2013 | Zhang |
| 2013/0223673 A1 | 8/2013 | Davis |
| 2013/0301932 A1 | 11/2013 | Massoudi |
| 2014/0003727 A1 | 1/2014 | Lortz |
| 2014/0029809 A1 | 1/2014 | Rhoads |
| 2014/0052555 A1 | 2/2014 | MacIntosh |
| 2014/0091985 A1 | 4/2014 | Birch |
| 2014/0108020 A1 | 4/2014 | Sharma |
| 2014/0119593 A1 | 5/2014 | Filler |
| 2014/0152874 A1 | 6/2014 | Clayton |
| 2014/0164124 A1 | 6/2014 | Rhoads |
| 2014/0244514 A1 | 8/2014 | Rodriguez |
| 2014/0304122 A1 | 10/2014 | Rhoads |
| 2014/0324642 A1 | 10/2014 | Winkel |
| 2014/0344118 A1 | 11/2014 | Parpia |
| 2014/0357312 A1 | 12/2014 | Davis |
| 2014/0363264 A1 | 12/2014 | Gowa |
| 2015/0016664 A1 | 1/2015 | Rodriguez |
| 2015/0039443 A1 | 2/2015 | Soon-Shiong |
| 2015/0046299 A1 | 2/2015 | Yan |
| 2015/0049902 A1 | 2/2015 | Moraleda |
| 2015/0052027 A1 | 2/2015 | Pavani |
| 2015/0054620 A1 | 2/2015 | Graube |
| 2015/0057917 A1 | 2/2015 | Cheng |
| 2015/0088701 A1 | 3/2015 | Desmarais |
| 2015/0088703 A1 | 3/2015 | Yan |
| 2015/0117788 A1 | 4/2015 | Patel |
| 2015/0123973 A1 | 5/2015 | Larsen |
| 2015/0139536 A1 | 5/2015 | Jin |
| 2015/0156369 A1 | 6/2015 | Reed |
| 2015/0168538 A1 | 6/2015 | Bradley |
| 2015/0193909 A1 | 7/2015 | Maayan |
| 2015/0199942 A1 | 7/2015 | Mochizuki |
| 2015/0248592 A1 | 9/2015 | Wang |
| 2015/0262116 A1 | 9/2015 | Katircioglu |
| 2015/0294333 A1 | 10/2015 | Avegliano |
| 2015/0302543 A1 | 10/2015 | Weaver |
| 2015/0310601 A1 | 10/2015 | Rodriguez |
| 2015/0324725 A1 | 11/2015 | Rosebery |
| 2015/0353758 A1 | 12/2015 | Weber |
| 2015/0363758 A1* | 12/2015 | Wu ..................... G06V 30/414 705/20 |
| 2015/0365660 A1 | 12/2015 | Wu |
| 2016/0027159 A1 | 1/2016 | Amirghodsi |
| 2016/0044460 A1 | 2/2016 | Cornaby |
| 2016/0119540 A1 | 4/2016 | Wu |
| 2016/0171336 A1 | 6/2016 | Schwartz |
| 2016/0171429 A1 | 6/2016 | Schwartz |
| 2016/0180533 A1 | 6/2016 | Pavani |
| 2016/0217547 A1 | 7/2016 | Stach |
| 2016/0253794 A1 | 9/2016 | Shekar |
| 2016/0275639 A1 | 9/2016 | Holub |
| 2016/0309082 A1 | 10/2016 | Maayan |
| 2016/0321518 A1 | 11/2016 | Shekar |
| 2017/0024806 A1 | 1/2017 | High |
| 2017/0032311 A1 | 2/2017 | Rizzolo |
| 2017/0124508 A1 | 5/2017 | Wasilewsky |
| 2017/0178310 A1 | 6/2017 | Gormish |
| 2017/0178372 A1 | 6/2017 | Gormish |
| 2017/0193324 A1 | 7/2017 | Chen |

(56) References Cited

U.S. PATENT DOCUMENTS

| | | |
|---|---|---|
| 2017/0193434 A1 | 7/2017 | Shah |
| 2017/0249491 A1 | 8/2017 | MacIntosh |
| 2017/0278057 A1 | 9/2017 | Itou |
| 2017/0286773 A1 | 10/2017 | Skaff |
| 2017/0286805 A1 | 10/2017 | Yu |
| 2017/0286901 A1 | 10/2017 | Skaff |
| 2017/0293959 A1 | 10/2017 | Itou |
| 2017/0357939 A1 | 12/2017 | Jones |
| 2018/0005176 A1 | 1/2018 | Williams |
| 2018/0108134 A1 | 4/2018 | Venable |
| 2018/0251253 A1 | 9/2018 | Taira |
| 2018/0257228 A1 | 9/2018 | Tingler |
| 2018/0293543 A1 | 10/2018 | Tiwari |
| 2019/0030713 A1 | 1/2019 | Gabardos |
| 2019/0034864 A1 | 1/2019 | Skaff |
| 2019/0149725 A1 | 5/2019 | Adato |

OTHER PUBLICATIONS

Image Segmentation article archived by Wikipedia, May 15, 2015.
Image Stitching article archived by Wikipedia, Feb. 25, 2015.
Japanese patent publication JP2011045502, Mar. 10, 2011, with machine translation.
Kejriwal et al, Product counting using images with application to robot-based retail stock assessment, 2015 IEEE International Conference on Technologies for Practical Robot Applications (TePRA) May 11, 2015 (pp. 1-6).
Kumar et al, Remote retail monitoring and stock assessment using mobile robots, 2014 IEEE International Conference on Technologies for Practical Robot Applications (TePRA) Apr. 14, 2014 (pp. 1-6).

\* cited by examiner

FIG. 6

| IDENTIFIER | AISLE | SHELVING UNIT/SHELF | POS'N | GTIN | PRODUCT NAME | PRICE | PRODUCT WIDTH | DECODING INFO |
|---|---|---|---|---|---|---|---|---|
| ... | ... | ... | ... | ... | ... | ... | ... | ... |
| 38F5B901 | B | 2/3 | 0" | 0016000275270 | HONEY NUT CHEERIOS | $4.29 | 10" | |
| 38F5B902 | B | 2/3 | 1" | 0016000275270 | HONEY NUT CHEERIOS | $4.29 | 10" | |
| 38F5B902 | B | 2/3 | 2" | 0016000275270 | HONEY NUT CHEERIOS | $4.29 | 10" | |
| ... | ... | ... | ... | ... | ... | ... | ... | ... |
| 38F5B920 | B | 2/3 | 19" | 0016000275270 | HONEY NUT CHEERIOS | $4.29 | 10" | |
| 38F5B921 | B | 2/3 | 20" | 016000275195 | CINNAMON TOAST CRUNCH | $3.99 | 10" | BLUE CHANNEL IF BACK OF SHELF |
| 38F5B922 | B | 2/3 | 21" | 016000275195 | CINNAMON TOAST CRUNCH | $3.99 | 10" | BLUE CHANNEL IF BACK OF SHELF |
| ... | ... | ... | ... | ... | ... | ... | ... | ... |
| 38F5B948 | B | 2/3 | 47" | 016000275393 | OATMEAL CRISP | $4.19 | 11" | EXTRA RED ILLUM. |
| 38F5B949 | B | 3/3 | 0" | 016000275393 | OATMEAL CRISP | $4.19 | 11" | EXTRA RED ILLUM. |
| 38F5B950 | B | 3/3 | 1" | 016000275393 | OATMEAL CRISP | $4.19 | 11" | EXTRA RED ILLUM. |
| ... | ... | ... | ... | ... | ... | ... | ... | ... |

FIG. 10

|     |     |
| :-: | :-: |
| (6) | (12) |
| (5) | (11) |
| (4) | (10) |
| (3) | (9) |
| (2) | (8) |
| (1) | (7) |

|     |     |
| :-: | :-: |
| (6) | (12) |
| (5) | (11) |
| (4) | (10) |
| (3) | (9) |
|     | (8) |

FRONT OF SHELF

IMAGE PROCESSING METHODS AND ARRANGEMENTS USEFUL IN AUTOMATED STORE SHELF INSPECTIONS

RELATED APPLICATION DATA

This application is a continuation of application Ser. No. 15/830,874, filed Dec. 4, 2017 (U.S. Pat. No. 10,552,933), which claims priority to provisional application 62/429,564, filed Dec. 2, 2016. This application is also a continuation-in-part of application Ser. No. 15/152,365, filed May 11, 2016 (U.S. Pat. No. 10,007,964), which claims priority to provisional applications 62/164,490, filed May 20, 2015, and 62/181,131, filed Jun. 17, 2015. The disclosures of these prior applications are incorporated herein by reference.

TECHNICAL FIELD

The present technology concerns image processing, e.g., in connection with analyzing imagery of store shelves captured by cameras conveyed by an autonomous robot.

INTRODUCTION

Retail shelf space is a limited resource. Placement of a product at eye level, near a top-selling national brand, can help make the product a best-seller. Lower shelf placement, near dog food and canning supplies, can make a product nearly invisible. For best returns, a retailer should design a store's layout to maximize impulse purchase of products having the highest profit margins per foot of shelf space. Factoring into this calculation are payments, or trade credits, that certain brands may pay a store in exchange for contractual promises to place particular products at particular prime locations.

Given the careful deliberations involved in designing store layouts, and associated contractual obligations, stores regularly check their shelves for compliance with intended shelf layouts. These layouts are commonly defined by "planograms"—maps depicting segments of shelving (commonly 4 feet in width by 6 feet in height) that specify which products are to be stocked on which shelves. Traditionally, store personnel manually checked shelves for compliance with planograms. This is a time-consuming, labor-intensive process.

A related task is checking that shelves are adequately stocked with inventory. Although point of sale cash register systems ideally track how much of each product has been sold, this information is not always a reliable indicator of shelf stock. (Some shoppers remove items from their carts and place them at random places in the store; some items are stocked both at end-cap displays and mid-aisle, so one location may be depleted while another is fully-stocked, etc.) Stocking is sometimes performed by delivery personnel for national brands, who may not scrupulously adhere to a store's planograms when stocking their products next to a competitor's products.

Recently, efforts have been made to automate some aspects of these tasks. For example, Bossa Nova Robotics offers a self-propelled robot, equipped with cameras and other sensors, which can traverse the aisles of a store every night. The sensors (including a depth-sensing camera system that yields 3D information) enable the robot to navigate, and capture imagery of every product on every shelf—including associated shelf tags, where present. Such imagery is downloaded to a server for analysis, which can identify certain products by image recognition and OCR techniques. After a night's imagery has been processed, the server can alert store management about shelf locations that need re-stocking. Aspects of the Bossa Nova technology are detailed in its patent publications 20170286773 and 20170286901. Simbe Robotics, Inc. and Imagine Robotics, offers competing products.

In accordance with certain detailed embodiments, digital watermark technology is employed to enhance the use of such shelf imagery, e.g., in inventorying stores, and assuring compliance with store planograms The foregoing and other features and advantages of the present technology will be more readily apparent from the following detailed description, which proceeds with reference to the accompanying drawings.

BRIEF DESCRIPTION OF THE DRAWINGS

FIG. 6 shows two cereal boxes, watermarked with blocks conveying block serial numbers, side-by-side on a shelf.

FIG. 10 shows an excerpt of a data structure with metadata associated with different shelf identifiers.

DETAILED DESCRIPTION

Figure 1B:
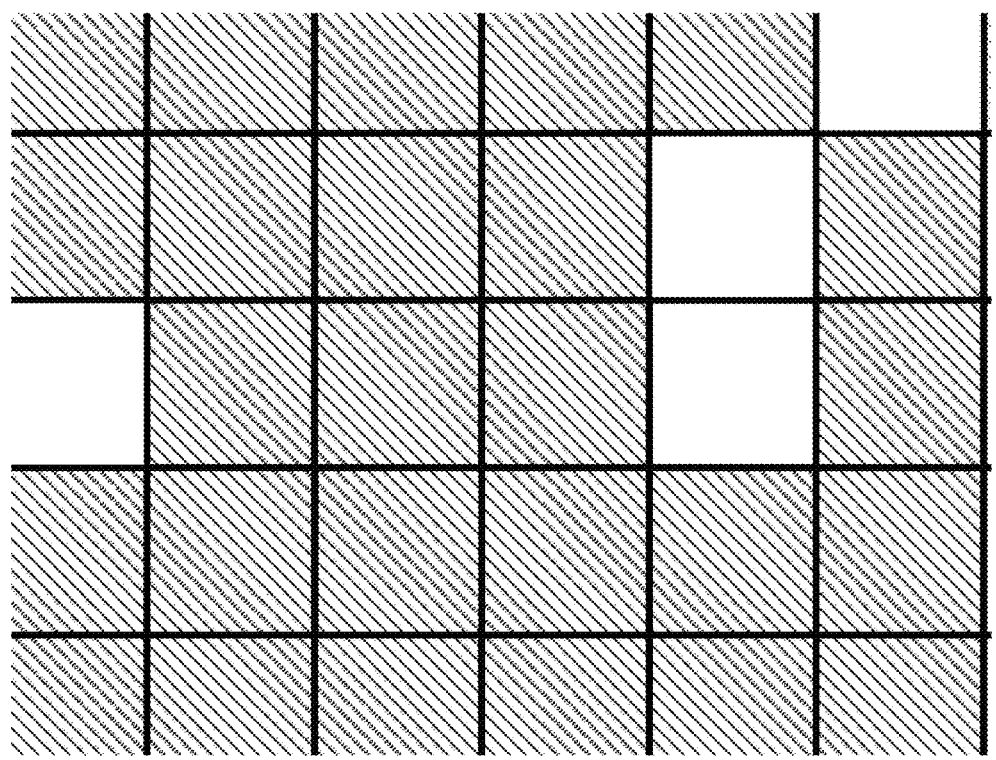
FIG. 1B indicates detection of some, but not all, of the FIG. 1A watermark blocks by a watermark decoder.

With 3D sensing technology, a store robot can discern the distance to each point within its field of view. The angular width of the camera's field of view is generally also known. This allows dimensions of objects within the field of view to be determined, based on their span in camera pixels. For example, if a robot camera is equipped with a lens having a horizontal field of view of 20 degrees, and the 3D sensor indicates an imaged product is 40 inches away, then the camera's field of view at a distance of 40 inches translates to $40*2*\tan(\theta/2)$ or 14.106 inches. If the camera sensor is 3240 pixels in width, then there are 230 camera pixels per inch of product face. Thus, if an object spans 1035 pixels, it is 4.5 inches in width.

Sometimes, the angular field of view is not precisely known. This can be the case, for instance, if the camera has a telephoto lens, and its field of view has not been precisely characterized for each possible zoom setting. In this case, a shelf label within the field of view can serve as a calibration tool. Such a label can be recognized by image recognition techniques (e.g., a generally rectangular shape, with mostly white on the left and mostly yellow on the right, with a barcode and text, and elongated in the horizontal direction with an aspect ratio of 5:2). The dimensions of shelf labels are often precisely known, e.g., because they are printed on feedstock of a known width (e.g., 4 inches).

If a shelf label is detected in camera imagery, its span—in pixels—can be determined. For example, if it spans 480 pixels, this indicates that there are 120 pixels per inch in the image plane occupied by the shelf label. The distance to the label is known from the depth-sensing camera system, as is the distance to a product further from the camera—on the shelf. The pixels-per-inch resolution varies inversely with distance. So if the ratio of the distance between the camera and the product, to the distance between the camera and the label, is 1.2 (call this ratio K), then the pixels-per-inch resolution at the product is 120/K, or 100 pixels per inch. If such a product has dimensions—in the image frame—of 250×450 pixels, this indicates its physical dimensions are 2.5"×4.5."

Such use of the shelf label as a calibration metric also enables the angular field of view at that zoom setting to be established. If the sensor is 3240 pixels across, and the four inch label spans 480 pixels, then this indicates that the full field of view at that image plane spans 4*3240/480, or 27 inches. If the label image plane is 20 inches distant from the camera, then the horizontal field of view is 2*arctan(27/(2*20)), or 68 degrees. Such information can be stored in a calibration memory, for the next time the lens is at that particular zoom setting (when a shelf label may not be available as a calibration reference).

Such photogrammetry becomes increasingly useful as retail packaging and shelf labeling includes hidden digital watermark data.

As is familiar from applicant's below-cited patent documents, digital watermarks commonly take the form of a square pattern, on the order of an inch or two on a side, which is repeatedly tiled across a printed surface. The watermark payload may comprise 50 or 100 bits, and is typically processed with a forward error correction process (e.g., turbo, Reed-Solomon, BCH) to assure robust conveyance of data despite distortion and other error sources. This forward error correction process may yield a redundantly encoded output signal that includes, e.g., 16,384 elements. These elements have "1" or "0" values and are mapped to a 128×128 array of watermark elements ("waxels") in a single watermark block. If there are 75 waxels per inch (WPI), then each block is 128/75, or 1.7 inches on a side. If printed at 300 dots per inch resolution, each block is 512×512 pixels in size, and each waxel spans a 4×4 pixel area. Although the position, scale and orientation of the watermark blocks on product packaging substrate are known at the time of printing, this information is unknown when processing an image of a product captured by a camera. Yet this information must generally be sleuthed as part of the decoding process. The sleuthing process can be computationally-intensive—as detailed in the cited documents, and becomes more complex and time-consuming as the range of possible positions, scales, and orientations of the blocks increases. Such sleuthing can be shortcut by knowing the physical scale of the watermarked object depicted in the imagery.

If a robot's camera is close to a product (or is distant, but using a telephoto lens), a single block of watermarked packaging may span 800 pixels (e.g., in the case of a single box of cereal that spans more than a full image frame). If the camera is remote from a product (or is close, but using a wide angle lens), a single block of watermarked packaging may span just 130 pixels (e.g., in the case of a can of tomato paste that spans less than a twentieth of the image frame). An exemplary sleuthing process can decode a watermark over a 4:1 scale variation (e.g., 50% to 200% of original scale, representing imaged block sizes of between 256×256 and 1024×1024 pixels). To cope with the 6:1 range in possible watermark scales (or larger) that may be encountered in shelf reading applications, however, requires extraordinary measures.

One approach is to apply a watermarking decoding process to each image two or more times, e.g., once at its original scale, and once again after interpolating the image to zoom by a factor of three. In the former case, the just-noted cereal box presents watermark blocks of 800×800 pixels to the decoder—within the 50%-200% reading range of the 512×512 resolution of the original block. In the latter case, the just-noted tomato paste can presents zoomed-in watermark blocks of 130*3, or 390×390 pixels to the decoder—again within the 50%-200% reading range of the original block. Such brute-force technique will successfully decode watermarks at an extended range of scale states, but considerably increases the amount of time that is required to extract watermark data from shelf imagery.

In accordance with a further aspect of the present technology, the above-noted photogrammetry techniques are employed to determine the number of pixels per inch for a product depicted within a captured image frame (e.g., based on viewing distance). The image is then re-scaled to put this metric at, or near, a target value (e.g., 300). For example, if a camera is found to sample product artwork at 230 pixels per inch (as in an earlier example), the image can be zoomed (interpolated) by a factor of 300/230, to yield an image in which the watermark is represented at a resolution of 300 pixels per inch (which corresponds to a watermark block of 512×512 pixels).

One embodiment uses a shelf label as a reference. If, as in the foregoing example, a four inch shelf label is 480 pixels in width, this indicates a sampling pitch of 120 pixels per inch at that image plane. If the ratio of the camera-product distance to the camera-label distance is K, the product is depicted with a resolution of 120/K pixels per inch. To restore the product artwork to 300 pixels per inch, the analysis processor enlarges (zooms) the image by a scale Z=300K1120. In the earlier example where K=1.2, the needed zoom factor is 3.

Thus, by simple operations involving the pixel-width of the shelf label, and the ratio of distances (camera-product and camera-label), shelf imagery can be quickly rescaled to a resolution that is optimum for watermark decoding. A brute-force trial of two (or more) watermark decoding operations is no longer required.

Moreover, a simpler (and thus faster) watermark decoder—one that can cope with, e.g., a reduced 1.5:1, or 2:1 range of scale states (instead of 4:1), can be used. The more accurate the rescaling of the imagery towards a 300 pixel-per-inch nominal value, the narrower the range of scale states that must be accommodated. A 2:1 range is sufficient if the image rescaling causes depiction of a single physical inch on the product to be spanned by somewhere between 212 and 424 pixels. A 1.5:1 range is sufficient if a single physical inch on the product is depicted as a span of between 245 and 367 pixels.

Figure 1A:
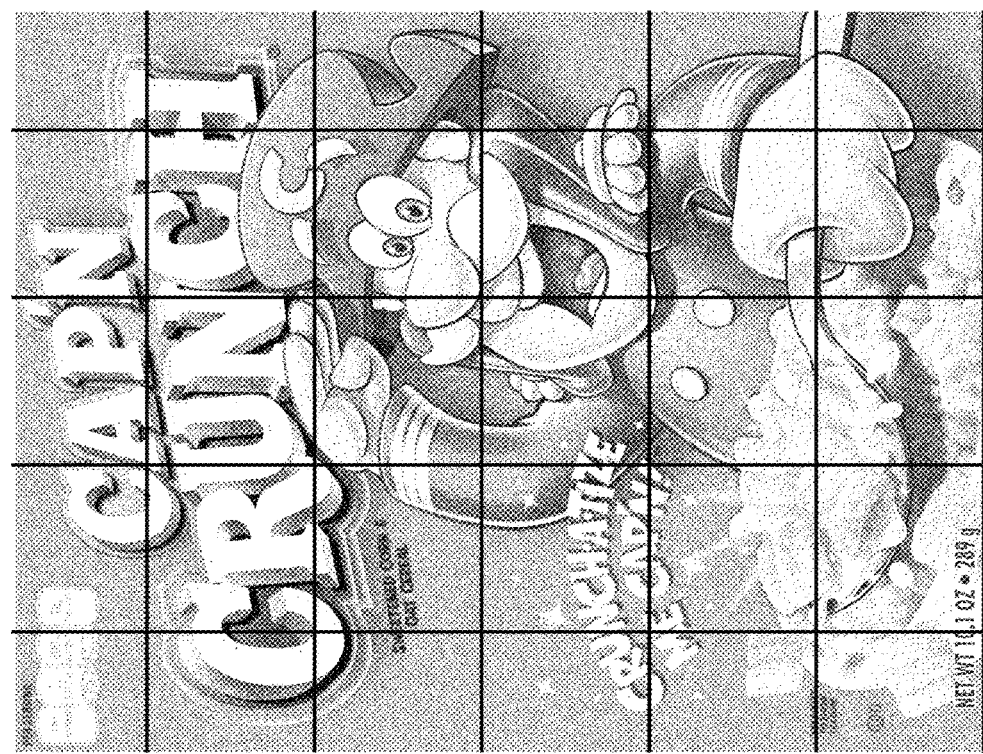
FIG. 1A shows locations of watermark blocks on a retail product.

FIG. 1A shows an illustrative arrangement of watermark blocks on product artwork. (The blocks do not align with the depicted face of the box because, in this example, tiling of the blocks started in the upper left corner of the printed carton blank. Parts of certain blocks are thus around a corner of the visible face.) In this embodiment, all of the blocks convey an identical payload.

When such a product is imaged by a robot, not all of the blocks may be decoded. This may be due to glare, an occlusion, or other factor. However, the blocks all carry the same payload (e.g., identifying the product by its GTIN identifier), so no information is lost. FIG. 1B shows—in cross-hatching—the blocks from which GTIN data is successfully decoded.

It will be noted that the decoded blocks share common edge boundaries. That is, where two blocks are proximate, they meet along a common boundary edge. There is no gap between blocks. Where a block is not decoded, the spatial gap left between nearby decoded blocks is in an increment of an integral number of block sizes. Such an array of decoded blocks may be termed "geometrically consistent."

Geometrical consistency is useful in distinguishing multiple instances of identical products arrayed side-by-side on a shelf. If two or more blocks are geometrically consistent, they originate—with a high degree of probability—from the same instance of a product. If two blocks are not geometrically consistent (i.e., they are geometrically inconsistent), they originate—with a high degree of probability—from different instances of the product.

Figure 2A:
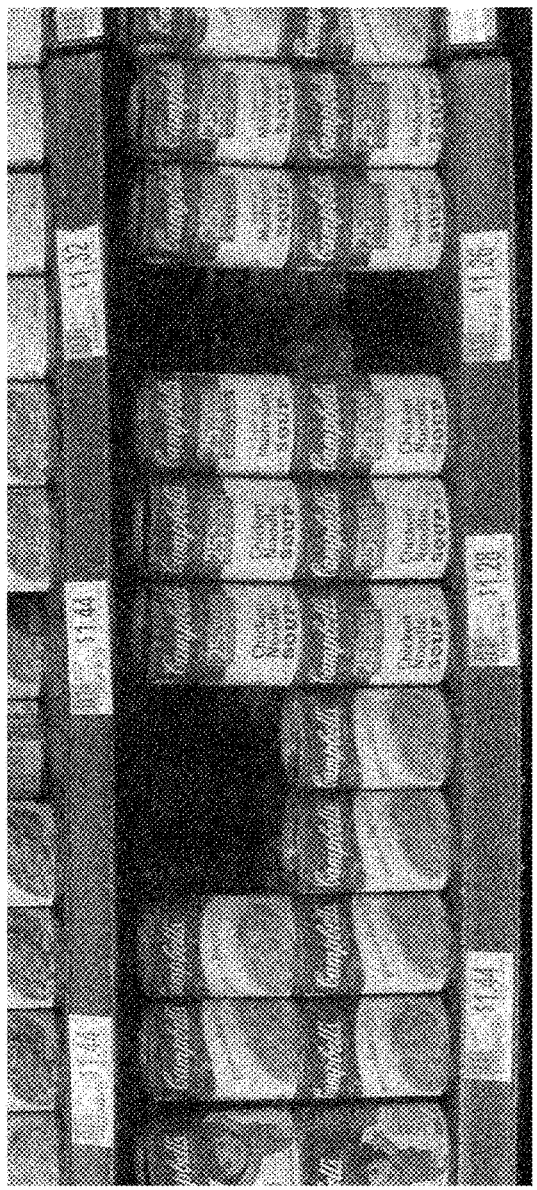
FIG. 2A shows an image of a supermarket shelf.
Figure 2B:
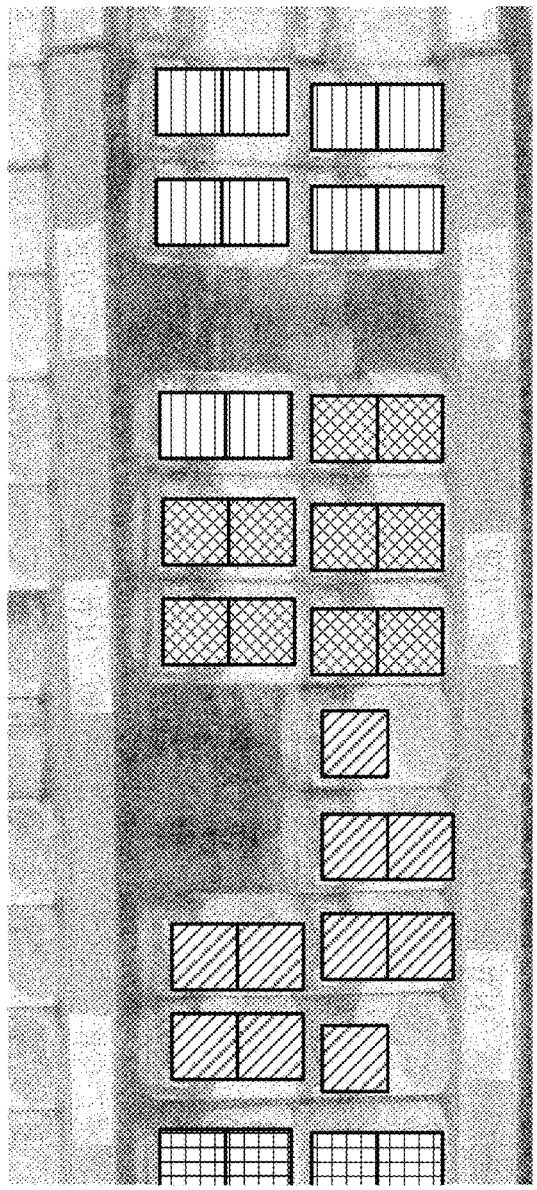
FIG. 2B shows, overlaid on the FIG. 2A image, detection of certain watermarked blocks from product labels.

This is illustrated by FIGS. 2A and 2B. FIG. 2A shows an excerpt of a robot-captured image depicting a shelf of soup cans. FIG. 2B is the same image, but showing (by overlaid boxes) the locations of watermark blocks decoded by the server that performs watermark decoding on robot-captured imagery. The different cross-hatch patterns indicate the different GTINs encoded by watermarks on the different products, e.g., chicken noodle soup vs. cream of mushroom soup. (In this example, a few blocks on the lower row of cans were not decoded.) No gap between decoded blocks on different cans is an integral multiple of a block dimension.

As noted, each block may take the form of a 512×512 pixel area, at 300 dpi. The watermark decoder can commonly resolve the location of each block to within a fraction of a pixel width (e.g., to within 0.5, or more typically 0.1, pixels). So even if a gap between decoded blocks is found to be 1025.1 pixels, such blocks can correctly be determined to originate from different objects.

In a particular embodiment, the system designer establishes a threshold deviation from perfect block alignment that is still regarded as geometrically consistent. For edge-adjoining blocks, the threshold may be within 0.5 pixels, or within 1 pixel. For gap-separated blocks, the threshold may be set, e.g., in the range of 1-5 pixels, plus an integral number of blocks. Thus, if the latter threshold is set at 1.5, then a gap between proximate decoded blocks of between 510.5 and 513.5 pixels, or between 1022.5 and 1025.5 pixels, would still be regarded as geometrically consistent. In contrast, a gap of 1025.6 pixels would indicate the blocks were decoded from different instances of the product.

(It will be recognized that the apparent width of a watermark block will depend on orientation of the product surface, relative to the camera's focal plane. For example, if a box is askew on a shelf, not squarely facing the aisle, the imaged width of a square watermark block on the product artwork will appear to be shortened horizontally, relative to its vertical extent. The angle at which the box is skewed can be determined by pose parameters sleuthed during watermark decoding. Alternatively, the product pose can be assessed, more roughly, from 3D depth sensing camera data. In either event, corresponding adjustments can be made. Likewise for product artwork on cylindrical product packages.)

As noted, shelf labels may be digitally-watermarked. The watermark can indicate the GTIN of the product with which each label is associated, and may also include a flag bit or other information so the shelf label watermark can be distinguished from the watermark on the associated product itself.

Such shelf labels can be used as visual beacons, or landmarks, in captured imagery, signaling store location—in a product sense. For example, a shelf label may indicate a Campbell's Chicken Noodle Soup region of shelving. This identifier—in conjunction with the store's planogram—may indicate that the imagery is taken from aisle 7B (i.e., the north side of aisle 7), 42 feet from the east end, on the 3d shelf (numbered from the bottom).

Store practice may be to position a shelf label at the left edge of each product region. The planogram may indicate that the product region for Campbell's Chicken Noodle Soup is to be eight inches in width—enabling stocking of three adjacent cans of soup, where each can is 2.625" in diameter by 4" tall.

As before, watermarking of the shelf label allows position of the label within the imagery to be determined to within a fraction of a pixel. (Between two and three watermark blocks may be tiled across the label, with the origin of one block in the upper left corner.) This allows the robot-captured imagery to be analyzed to determine whether the stocked inventory matches the planogram.

Figure 3A:
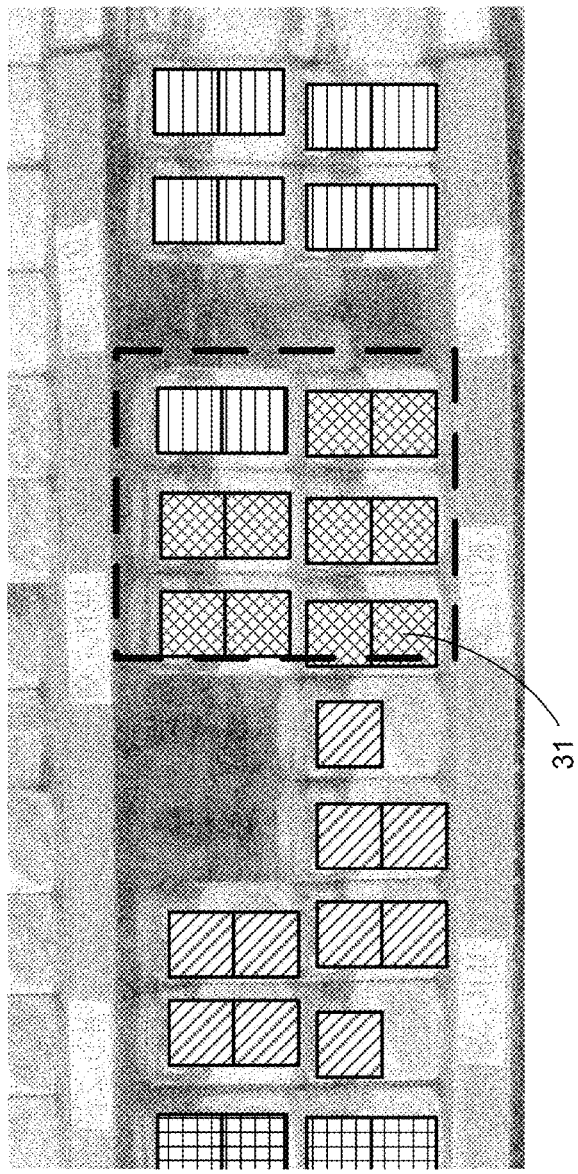
FIG. 3A shows how a shelf label can be used to define a product region on a store shelf, per a store planogram.

Referring to FIG. 3A, the left edge of the Campbell's Chicken Noodle Soup shelf label serves as the left edge of an overlaid dashed bounding box that extends eight inches to the right, and the full height of the shelf space. Again, the known width of the shelf label can serve as a measuring reference. That is, the bounding box has a width (in pixels of captured imagery), equal to the width of the shelf label (in pixels), times the ratio of the product region width to the label width.

After the bounding box is virtually located in the captured FIG. 3A imagery, the server checks the watermark data. In the FIG. 3A case, the watermarks show 6 cans of soup within the bounded area (as indicated by 6 different instances of non-geometrically consistent product watermarks found within the box). However, one of the watermarks indicates the can is of Cream of Mushroom soup—not Chicken Noodle soup. This error is added to a punch list of planogram exceptions that results from the analysis. A store employee uses the punch list to make needed corrections to product placements.

(Some "slop" of product placement is commonly permitted. In one embodiment, a product item is regarded as properly placed if the center of each watermark block decoded from that item is within the associated bounding box. This assures that the slop is less than half a watermark block in extent, or less than 0.85 inches. Thus, the fact that watermark blocks for the left-most, bottom can of Campbell's Chicken Noodle Soup are found to extend beyond the left edge of the FIG. 3A bounding box, is not regarded as a problem.)

Figure 3B:
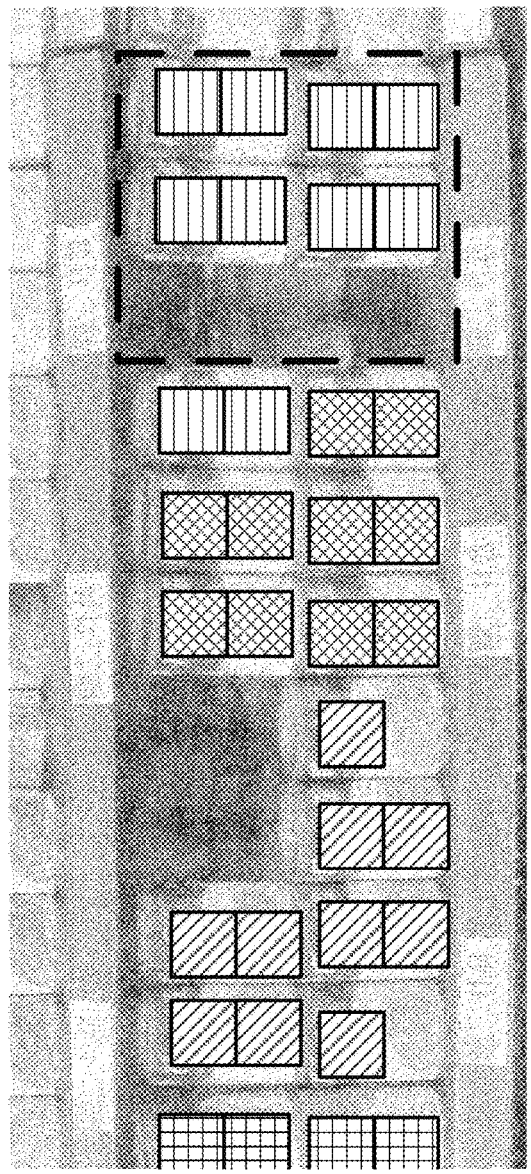
FIG. 3B is like FIG. 3A, but shows a different product region.

In like fashion, the rest of the shelf is similarly analyzed. FIG. 3B depicts analysis of the next product region to the right, which is an eight inch segment of shelf that is planogram-assigned to Campbell's Cream of Mushroom Soup. Analysis of this region of the captured imagery shows only four cans of such soup (by detection of four watermark patterns that are not geometrically consistent). All indicate the expected variety of soup. So the punch list simply instructs the store employee to restock cans of Campbell's Cream of Mushroom Soup in the noted region.

While the just-discussed arrangement located assigned product regions by reference to shelf labels, in other embodiments other approaches can be used. For example, a robot may track its position using other known locating technologies, such as graticule markings printed on the floor, dead reckoning from gyroscopes or other position sensors, wireless triangulation, RFIDs and other wireless beacons, GPS, etc. Knowing its location, the robot can consult a database containing store layout information, to determine the planogram-assigned product placement for any location in the store. (Such other location techniques are also useful in establishing that the shelf labels are placed at positions expected by the store planogram.)

Shelf labels can also serve to trigger position-dependent actions by the robot. For example, as a robot is navigating its way along an aisle—capturing imagery of adjacent shelving, a shelf label may cause the robot to change its illumination source to better capture data from a certain type of product. For instance, the spectrum or intensity of the illumination may be changed. Similarly, a shelf label can trigger a change in speed, causing the robot to speed up or slow down. Likewise, a shelf label can cause the robot to activate (or de-activate) a particular sensor, such as a near field (RFID) detector, or a camera adapted to capture imagery at an unusual elevation (different than the shelves normally-imaged). Still further, a shelf label may cause a camera to switch imaging modes, such as frame rate, resolution, aperture, white balance correction, type of image compression, imaging spectrum, etc.

In such embodiments, analysis of at least certain captured imagery is performed in real-time, while the robot is transiting the store (rather than in an offline mode, after the full store has been traversed). Each frame of imagery is examined, e.g., by a GPU configured as a stream processor, to identify rectangular features of a certain range of pixel scales, with a 5:2 aspect ratio. These regions can be segmented-out, and applied to a watermark decoder. The resulting shelf label payload is checked against a list of action-triggering label payloads stored in a data structure. If a match against the stored list is found, then an action stored in association with that shelf label payload is undertaken (e.g., switching spectral illumination to activate an infrared LED light source).

(Such position-dependent actions can alternatively be triggered in response to detection of certain product items, or wireless beacons, or RFID chips, etc.)

The type of camera(s) with which the robot is equipped may be of various types. One captures a static frame every increment of time or distance (e.g., every two seconds of time, or every 28 inches of robot travel). In other embodiments, a 1D imager is used, and captures successive lines of vertical imagery as the robot travels—thereby, in the aggregate, capturing lengthy strips of imagery. Sometimes a single imager is employed, and is switchable between any of these modes.

In the static frame case, the frames may be stitched together to yield a panorama-like strip depicting many feet—up to a full aisle—of shelving. However, traditional image-stitching technologies rely on matching of image keypoints (such as Harris corners, SIFT points, etc.). Since store shelving often includes multiple instances of identical products, the keypoints may become confused. For example, a stitch boundary reliant on Harris corners in the stylized script of the Campbell's logo on soup cans is prone to confusion, since there may be many identical presentations of such logo in the images being stitched.

In accordance with another aspect of the technology, the gaps between detected watermark blocks serve as distinctive features that enable corresponding locations to be identified in two or more pictures.

As noted, watermark detection involves determining the location of each watermark block to within sub-pixel accuracy within an image. As a consequence, the gaps between detected blocks can be determined with similar accuracy.

Figure 4A:
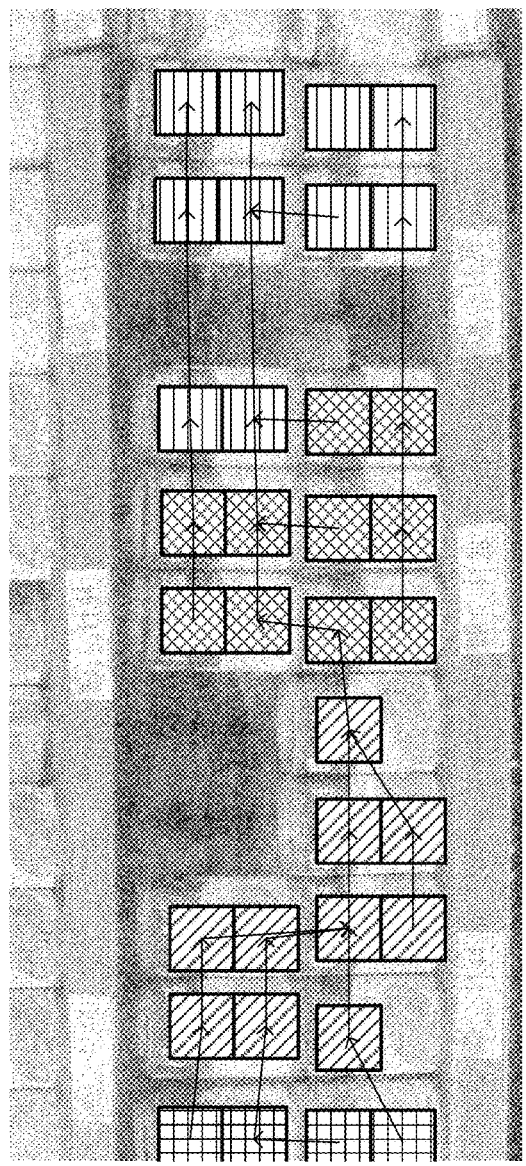
FIG. 4A shows how detected location of watermark blocks in FIG. 2B can be used to form a fingerprint of a shelf, by which the shelf can be recognized, and by which distinctive features (e.g., for image stitching and augmented reality overlays) can be defined.
Figure 4B:
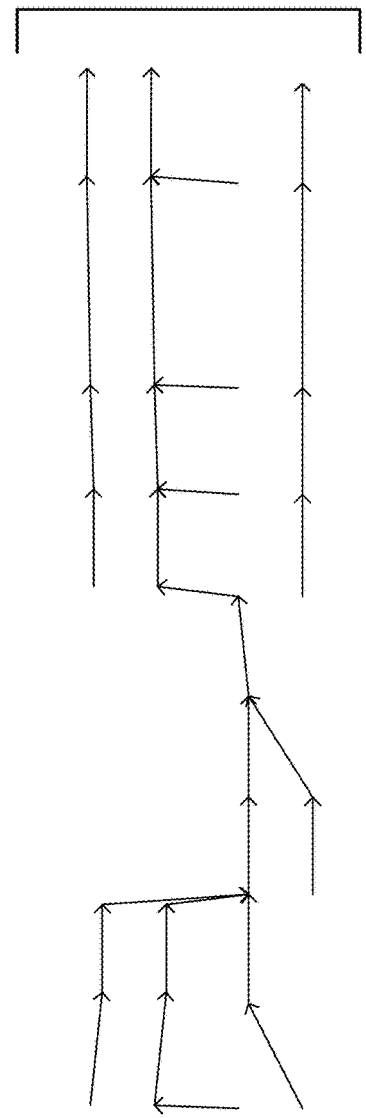
FIG. 4B is like FIG. 4A, but without the underlying image.

An illustrative embodiment defines a vector between the center of each decoded watermark block, and the center of the nearest non-geometrically consistent watermark block whose center is to the right. Such an arrangement is shown in FIG. 4A. FIG. 4B is identical, but without the image and watermark block overlay.

Although several of the vectors look to be of the same length, a single pixel translates to about a three-hundredth of an inch. So sub-pixel resolution allows spatial variations of this order—or better—to be distinguished. Moreover, even if soup cans are packed perfectly uniformly side to side, the position of the watermark in the imagery also depends on the precise rotation of the can. The periphery of a soup can is about 8.25 inches, or 2475 printed pixels. The product label will appear to shift one pixel width to the right or left in the captured imagery with a rotational variation of just one-sixth of an angular degree. Since the cans are placed by humans, variations one or two orders of magnitude greater than this are commonplace. (That said, where two blocks are detected on each of two horizontally-adjoining items, it is not unusual for the two resultant vectors to have the same lengths and orientations.)

Figure 5:
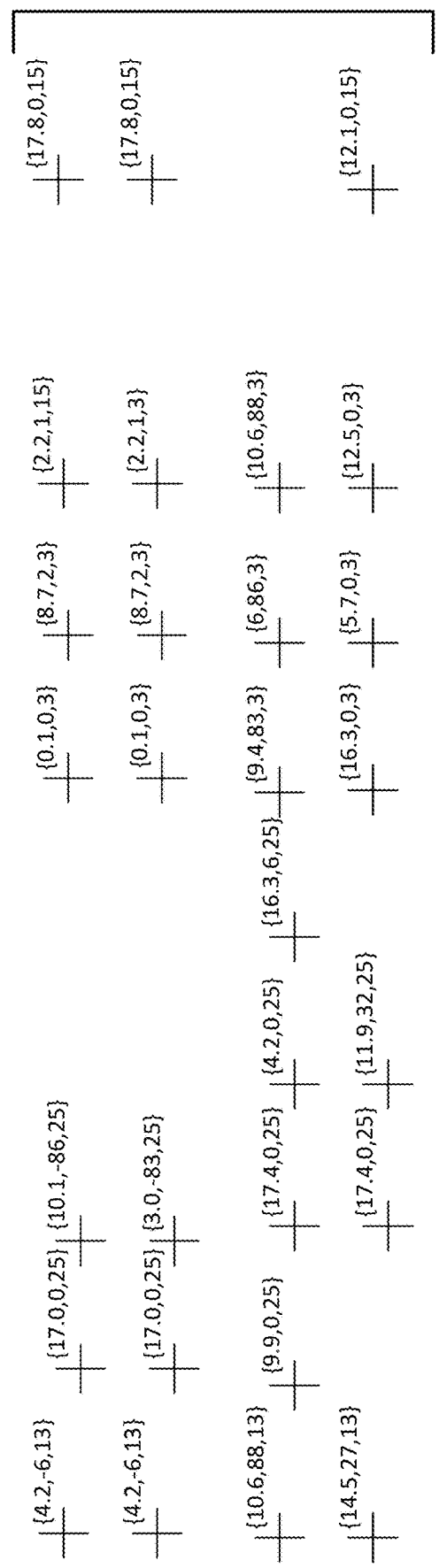
FIG. 5 shows triples of data associated with differently-located watermark blocks in FIG. 4A.

In a simple embodiment, the center of each decoded watermark tile is assigned a datum equal to the pixel length of the vector having that center as its origin, and the center of the next-to-the-right pixel tile as its terminus. A modulus operation (e.g., modulus 20 pixels) may be performed to aid in feature matching. In another embodiment, the center of each tile is assigned a pair of data: a vector length metric as above, and also a datum indicating the angular orientation of the vector. In still another embodiment, the feature data includes a third element: the payload of the watermark (or a subset of its bits), yielding a triple of data. Such an arrangement is shown in FIG. 5 (magnified somewhat to allow room for the feature point legends).

The pattern of such locations serves as a sort of fingerprint for a shelf. The locations themselves (e.g., at centers of watermark blocks) can be analogized to keypoints in the captured imagery.

Constellations of such keypoints can be used in ways familiar with other image keypoints—such as SIFT and SURF keypoints. For example, overlapping images can be virtually stitched together by reference to such keypoints. (That is, the keypoints permit location of identical points in different images, permitting the images to be combined in registered alignment.)

In one arrangement, such keypoint data are determined for two different images, and a pixel offset between the two images is determined that results in a greatest degree of match (or a minimum degree or error) between the spatiallyassociated vector data. Transformations other than translation can be similarly determined, e.g., to correct for slightly different scales between two images, or slight rotation of one image relative to the other.

By accurately stitching together plural frames of imagery, by reference to keypoints—whether of the sort just-detailed, or of more conventional varieties (keypoints are sometimes termed "salient points"), a truthful depiction of inventory conditions can be realized. Counts can be based on such stitched imagery without concern about double-counting (e.g., when the same item(s) is depicting in two image frames—captured when the moving robot was in two different positions in the aisle, but with overlapping fields of view).

By identifying keypoints on shelves, the present technology also allows accurate identification of repeated depictions of the same items across multiple images, even if stitching is not involved. That is, the processing system can visually determine that a certain region of shelving is depicted twice (or more) in the image collection because the same distinctive fingerprint pattern, based on product arrangement minutiae (as just-discussed) is found to be in common between two (or more) images. The duplicative region can be disregarded in all but one image frame, when performing inventory counting.

The above-described keypoints can be used as landmarks used in presenting an augmented reality overlay on imagery captured from a shelf (e.g., by a consumer smartphone or headworn apparatus). Likewise, overlay data or colors can be projected onto shelved products, by reference to such keypoints. (Such projection is detailed, e.g., in applicant's patent publication 20140052555.) The keypoints can also serve as spatial position markers, by which a camera-equipped device (e.g., smartphone, or robot) can reckon its precise location, relative to a shelf in a store, and to items on the shelf.

(Naturally, the centers of the watermark tiles needn't be used as the keypoints. Any other point can similarly so-serve, e.g., the upper left corner of the tiles.)

Applicant's patent application 62/036,512, filed Aug. 12, 2014 (attached to priority application 62/181,131) discusses how watermarks can be used to resolve ambiguities in item count at supermarket checkouts. The application notes, "One challenge may occur if two or more of the same packaged items are within a single image frame. For example, 2 cans of diet Mountain Dew might be pictured in the same frame. The watermark detector finds a read, but in different, non-contiguous image areas. In such cases a watermark payload may be used to look up a spatial template. The spatial template is sized roughly to represent a particular item (e.g., diet soda). The spatial template is placed around a block area where watermarks were detected. If watermarks (or watermark components like orientation components) are located outside of the spatial template (or outside of a predetermined area or tolerance) then there is a likelihood that the image frame includes two or more watermarked objects."

A similar approach can be used to distinguish multiple instances of the same item stocked on store shelving.

In another arrangement, the computational burden of watermark decoding can be reduced by a related watermark-regeneration approach. Once a single watermark block has been decoded from captured imagery, a pure signal watermark block can be generated (regenerated) based on the decoded payload. (The pure signal refers to the watermark without any underlying product artwork). The system then applies a correlation detector to nearby parts of the imagery (e.g., within a distance of 5-50 watermark block-widths vertically and horizontally), searching for the presence of the same watermark pattern in other parts of the imagery. Image locations where the correlation is found to spike are known to have the same watermark blocks—indicating the same type of product. By such arrangement, detection of a single watermark block by conventional watermark decoding can lead to detection of a dozen or more nearby watermark blocks by simpler correlation operations, speeding processing.

Correlation is best suited for objects with planar faces. For curved cans, correlation becomes more difficult. Nonetheless, detection of one watermark in an image can still help shortcut detection of other watermarks in the image.

Returning to FIG. 3A, each shelf label denotes the beginning of a new stock region on the shelf. If shelf imagery is processed from left to right (and from bottom to top), then detection of a new shelf label can signal the watermark detector to be alert for a new product, and a new watermark. The detector thus applies a conventional detection operation.

However, once a first watermark block has been detected (e.g., block 31 in FIG. 3A, from a can of chicken noodle soup), the detector can switch modes. The detector now knows something about the watermark it's looking for: it knows its likely payload. If one can of chicken noodle soup is detected, it is more likely than not that the next product detected will also be a can of chicken noodle soup. So rather than examine adjoining imagery to determine which of a nearly unlimited universe of product watermarks is present, the detector tackles the easier task of determining whether a watermark having a particular payload is present. The just noted watermark regeneration and correlation approach can be employed. Alternatively, the detector can start its search for this probably-known watermark in a conventional manner, but with a good idea of the watermark's scale, and its placement ("translation") in the vertical dimension of the imagery. If the sought-for particular watermark is not detected, the detector can fall back to the customary open-ended task for decoding a watermark—of any payload and/or scale state/location. Yet because there are commonly several instances of each product on the shelf, a net computational saving is achieved.

Figure 7:
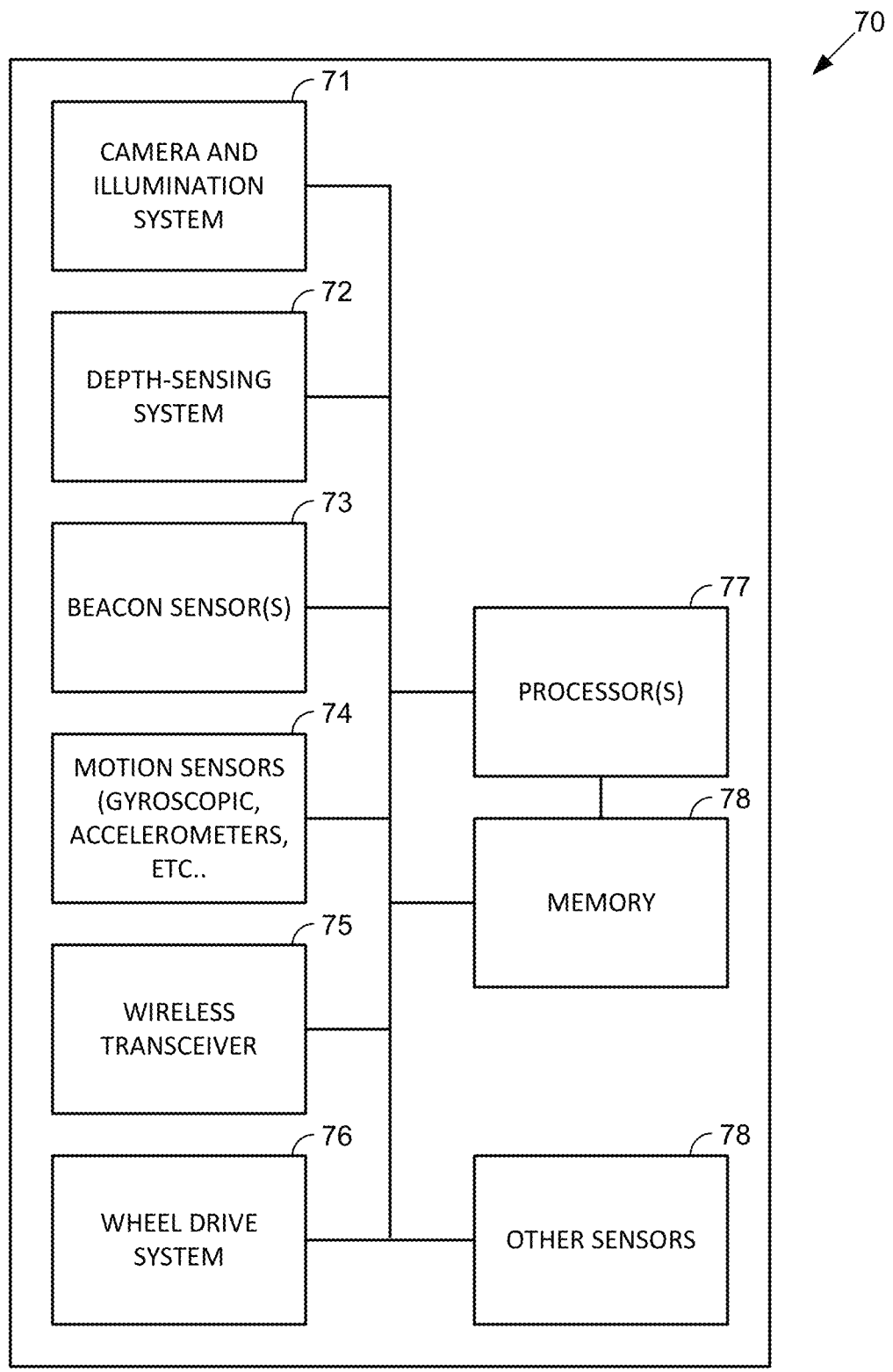
FIG. 7 depicts a hardware embodiment of the present technology.

FIG. 7 depicts an illustrative hardware implementation of the present technology. Shown is a mobile robot 70 that includes a camera/illumination system 71, a depth-sensing system 72 (which may form part of camera system 71), one or more beacon sensors 73, gyroscopic sensors 74, a wireless transceiver 75, a wheel drive system 76, and one or more processors 77 configured by software instructions stored in a non-transitory memory 78. Naturally, a variety of other sensors 79—some mentioned above, can also be included for navigation, product identification, robot stabilization, etc.

It will be recognized that the arrangements described above aid in inventorying stores, and assuring compliance with store planograms, with speeds and accuracy much greater than is humanly possible. For example, watermark-based product identification is essentially 100% accurate, and a robot can gather imagery from shelving on one side of a typical grocery aisle in less than two minutes. Use of watermark item identification enables operation without positioning stock so that unsightly barcode markings face the aisle.

FURTHER DISCLOSURE

Increasingly, retailers are using space atop the shelfing units—out of reach of many consumers (e.g., in some instances at 90 or more inches above the floor)—for stocking additional inventory. A store-inventorying robot can be equipped with one or more cameras to image this above-top-shelf region.

For stability and intimidation reasons, it may not be desirable to equip a robot with a body portion that is 80+ or 90+ inches tall. Instead, a narrower fixture can extend up from the main body of the robot, equipped with a lens and imaging sensor, to image at such elevated heights (e.g., between 72 and 92 inches). Alternatively, a periscope arrangement may be employed, with the imaging sensor on the main body, but looking out from an aperture that is higher, e.g., using a mirror arrangement. In still another configuration, a camera may be disposed at or near the top of the main robot body, and be pointed upward, at an angle $\Phi$ above the horizon, to image stock inventoried above the top shelf. Image processing software in the robot can compensate imagery captured with such an oblique view to remove the resulting perspective distortion.

In accordance with a further aspect of the technology, a robot is employed to help identify counterfeit merchandise. (Some products are often counterfeited; Duracell brand batteries are one example.)

Imagery captured by a robot can be analyzed to recognize a shelved product by its visual appearance. Image fingerprints, for example, can be derived from product artwork, and compared against reference fingerprint data for each item in the store (or for each item in the aisle, or shelving unit, where the robot is capturing imagery), to find a match, indicating the product identity. Other visual product recognition techniques can also be used, including color histograms and trained neural networks, etc.

Alternatively, if the product is correctly shelved—in proximity to a shelf label that includes textual or machine-readable data identifying the product, then the shelf label data can be used to identify the product. Still further, if a barcode is visible in imagery captured from the product, then it can serve to identify the product. RFID identification can also be employed.

With the product identified—by whatever means, a data structure is next queried to determine whether the artwork of that identified product should bear a digital watermark. (Some products do, some don't.) If the identification data indicates the product is a 4-pack of Duracell AA batteries, and the database indicates that packaging for the 4-pack of Duracell AA batteries should be watermarked, then failure to find a watermark in the captured image depiction of such product is a good indication that the product is counterfeit. (Counterfeiters commonly "re-originate" the packaging artwork for their wares. Such re-origination process commonly results in artwork lacking a proper watermark.)

As the robot navigates the store, it can examine each product in turn—identifying it by one of the noted means, and determining whether its artwork includes a watermark. For those that should include a watermark, but do not, the robot can compile a report identifying items in the store that are possibly counterfeit. The report may include a graphical depiction including a store shelf, with items that are possibly counterfeit presented in a first highlighted fashion (e.g., outlined in a bold, colored and/or dashed outline). With such report, store personnel can find the suspect product(s) and investigate further.

Some products may be marked with watermarks that encode, or link to, information including expiration date and/or manufacturing lot code. In its survey of a store, a robot can further use watermark information decoded from products to access expiration date information for each product so-marked. The referenced report, or another, can include information identifying products in the store that are past their expiration date (or within some brief interval before such date, e.g., a day or two, or a week). Again, a graphical depiction can be provided, in which such products may be flagged by distinctive highlighting.

In like fashion, if a manufacturer has issued a recall notice for products bearing a certain lot code (e.g., indicating a particular place and date of production), then the robot can use the watermark information decoded from products to determine if any shelved product is subject to such a recall. Again, the findings can be included in a report, e.g., with particular products graphically depicted and identified by distinctive highlighting.

In accordance with a further aspect of the present technology, a shelf is marked with a shelf label that is much longer than the tradition length (e.g., of 4 or 5 inches). For example, a shelf label may be one, or several, feet long. One particular shelf label according to the present technology is four feet long—the width of many popular shelving units. In other embodiments, a shelf label may run the full length of a store aisle, e.g., 50 or more feet in length.

The preferred elongated shelf label is characterized by plural different markings along its length, e.g., steganographic digital watermarks having the form of blocks. an inch or so on a side. Each marking encodes an identifier. Each serves as a visual beacon that can be sensed by a camera-equipped robot—helping to guide its navigation and/or other operation.

The encoded identifiers may literally encode product information, e.g., product names or GTIN identifiers. More commonly, however, the identifiers simply encode numbers—which may be arbitrary. For example, the numbers can each be a random number. Or they may be ordered in some fashion.

Figure 8A:
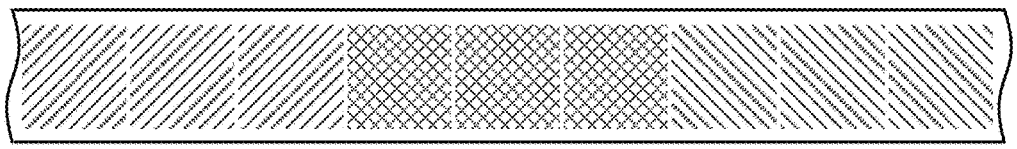
FIGS. 8A, 8B, and 8C show a few variants of how steganographically-encoded blocks can be arrayed along a shelf label.
Figure 8B:
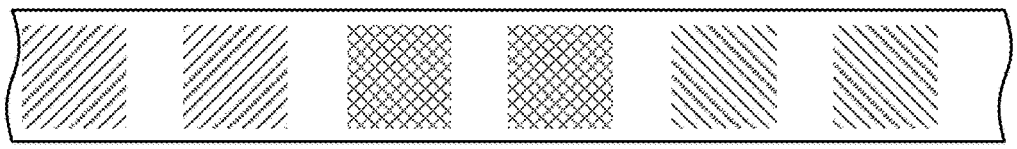
Figure 8C:
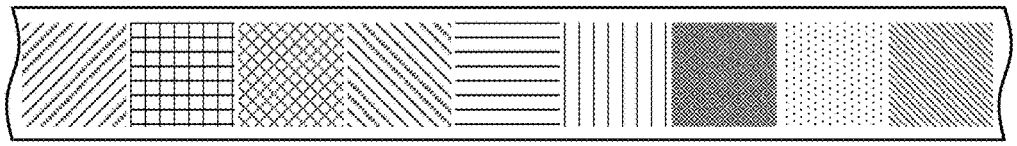

In one particular embodiment, there is a different identification marking (e.g., watermark block) every inch along the shelf label. In other embodiments, different indicia may appear every two, three or four inches along the label. FIGS. 8A-8C show illustrative arrangements. (For expository convenience, watermarks shown in these figures are perceptible. In actual practice, watermarks are generally imperceptible.)

Each of the depicted labels is an inch in height, and four feet in length. In FIG. 8A, a first watermark block—an inch square and encoding a first identifier—is repeated three times horizontally (edge to edge). A triple of a second watermark block—encoding a second identifier—then follows, starting three inches to the right of the start of the first watermark block. Next is a repeated third watermark block, etc.

In FIG. 8B, a first watermark block is repeated twice, in spaced-apart fashion (e.g., a half inch between the blocks), before being followed by second and third blocks in similar fashion.

In FIG. 8C, every linear inch of the shelf label conveys a different marking: first, second, third, fourth, fifth, etc., watermark blocks.

Figure 9:
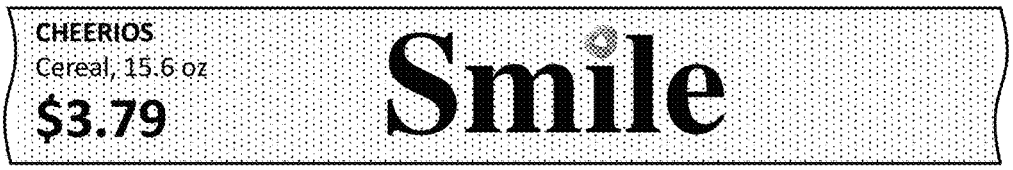
FIG. 9 shows an excerpt of an elongated steganographically-encoded shelf label, also printed to include human-visible text and promotional messaging.

Since watermark encoding on the elongated label is steganographic, text and graphics can be printed along the full length. FIG. 9 shows how such a label can be printed with human-readable product information, and also promotional/advertising messages. (Although only two such indicia are shown in FIG. 9, a two-foot, four-foot, or longer label can naturally be printed with many such indicia—each different, or some repeating.)

The identifiers encoded by the watermark blocks can be associated with metadata using a data structure, such as a table or database—stored in the robot memory or remotely (e.g., in a store server memory, or in the cloud), or both. FIG. 10 shows an excerpt of an illustrative data structure 100, corresponding to the shelf label of FIG. 8C. Table 100 thus provide different metadata for every inch of every shelf on every aisle in a store (and for every different store in a chain of stores). In other embodiments, of course, table 100 can provide data with different spatial granularity, such as every two, three, or six inches.

Depicted in table 100, in association with each identifier, are metadata including the aisle, shelving unit and shelf to which the identifier corresponds; the location on the shelf (starting with 0" at the left edge of the shelf, and continuing in one inch increments to 47" on the right end of the shelf, before the next shelving unit begins); the GTIN of the product that should be stocked at that location; the trade name of the product; its price; its width; special instructions that may be relevant to that location, etc.

It will be recognized that traditional planogram data is all in the table. With such a data structure, and the captured imagery, the robot can sense which products are out of place, or out of stock, and generate a punch list for attention by a store clerk to correct same. It performs the store planogram compliance checks that traditionally have been performed by store personnel.

Other information can also be stored in data structure 100. For example, some stores assign their own identifiers to products—in addition to the standardized GTIN. Information such as supplier identification, and scheduled promotions (e.g., a dollar off whipped cream the day before Thanksgiving) can also be stored.

Other business rule data may be also included. One such business rule is that, if stock of a particular item is depleted by N or more units from the usual fully-stocked complement, then dispatch a clerk with replacement stock. Another rule may specify that items should only be stocked to a depth of 6 inches back from the front edge of a shelf. If a product is detected more than that threshold distance back from the front edge of the shelf, it should be added to a clerk's punch-list to move the stock forward, e.g., to the front edge of the shelf.

Determining the number of units on a shelf can sometimes be difficult, because units near the front of the shelf hide other units behind. One way of dealing with this issue is to distinctly identify, e.g., by serialization, each of the units.

Supermarket stock commonly is provided in cartons, e.g., of a dozen or two dozen units. In some stores, the cartons are cut so as to leave a cardboard tray on which the units rest—allowing all units in the carton to be shelved quickly without much manual fuss. In other stores, a clerk may unpack units from the carton onto the shelf while maintaining the carton's spatial arrangement.

Figures 11A, 11B:
FIG. 11A is a top plan view of a freshly-cut 12-pack carton of breakfast cereal boxes.
FIG. 11B is a top plan view of the boxes of cereal from the carton of FIG. 11A, on a shelf, after three boxes of cereal have been removed.

FIG. 11A shows a top view of a carton containing a dozen boxes of breakfast cereal. The artwork for each box in the carton is digitally watermarked to include a serialized unit code, e.g., ranging from 1 to 12.

If the 12 boxes of cereal are shelved in the same arrangement—either on the carton base, or fully-removed from the carton, then the robot can read the serialized unit code from the front-most unit to determine how many boxes are missing. For example, in FIG. 11B, if a robot camera images the stock, and software decodes serialized unit code of "3" from the front box facing the aisle, then the system knows that units "1" and "2" from the arrangement are missing (and that units "4," "5," and 6" are probably arrayed behind the front unit) Likewise, if it decodes serialized unit code of "8" from the adjoining area, the system knows that unit "7" is missing (and that units "9," "10," "11," and "12" are likely arrayed behind). Thus, the system can determine that three of the 12 units are missing. (If the store's inventory system—based on counts of items checked-out and paid for at point of sale terminals—indicates that only one box of this cereal has been sold, then the discrepancy indicates a potential theft problem to which the system can alert store management.)

The number of units in each carton, and their numbering arrangement as a function of geometry, can be among the items of metadata associated with a product in the data structure of FIG. 10.

Some packages may benefit from special attention by the robot. For example, watermark encoding on a particular package may be encoded in a color channel from which it is most reliably detected by using a particular color of illumination. By reference to information accessed from data structure 100 (which, in turn, is accessed using an identifier decoded from the shelf label), the robot may be instructed to activate a supplemental illumination system comprising red LEDs as it captures imagery at a particular location along a particular shelf. (An exemplary robot may have a vertical array of a dozen cameras, spaced every 6 inches—each with an associated variable illumination system, allowing stock on different shelves to be illuminated and imaged with different parameters, in accordance with data in data structure 100.)

Similarly, the data structure 100 can inform the system as to the color channel(s) in which the watermark on a particular product is encoded. If data structure 100 indicates that a jar of spaghetti sauce stocked at a particular shelf location is watermark-encoded in the blue channel, then the system may disregard red and green channel data in decoding the watermark.

Just as the producer of the product (or its packaging) can provide metadata for table 100 about the color or intensity of illumination that should be applied, or the color channel that should be examined for watermark data, the producer can likewise provide grade information indicating a quality score for the encoded watermark. Some watermarks are easy to discern and read; others take a bit more analysis to find and decode. (Physically smaller items—such as baby food—may have relatively smaller regions encoded with watermark signal. This smaller expanse of signal may make it more difficult to locate within captured imagery, or may lead to a lower signal to noise ratio.)

Metadata in the table 100 can include such information, e.g., establishing a computational budget (e.g., in CPU processing cycles or milliseconds) that can be expended in watermark decoding at different regions of a shelf. The system may thus be allowed to spend an extra few milliseconds processing imagery to decode a watermark, if the table indicates the imagery at that location depicts a baby food jar having a lower watermark score.

Sometimes the watermark decoding clues stored in the data structure 100 may be applied conditionally based on other circumstances. For example, if an item is located towards the back of a shelf, the illumination there may not be as bright, and artwork details may be lost in shadows. Conversely, if the item is right at the front of a shelf, the normal illumination may over-expose the captured imagery, losing certain highlight details in the depicted artwork. Thus, the table 100 may indicate that the robot should apply different illumination, or a particular image channel should be analyzed, based on the position of the product on the shelf. (The position of the product on the shelf, e.g., flush with the front of the shelf, or pushed ten inches to the back, can be determined using available data, e.g., the scale of the watermark block, the table-indicated width of the physical product, and the number of pixels spanned by each of these elements in the captured imagery. A depth sensing camera can alternatively be used.) In some embodiments, not each shelf on a shelving unit has an elongated label as discussed above. Instead, there may just be one such label—running along the length of the unit (along a shelf, along the base of the unit, along the floor, or elsewhere). The robot, and data structure 100, can then identify particular shelves and product stock areas at each linear location, e.g., by their distance above the floor, or otherwise.

In such an embodiment, or others, the shelves may be equipped with electronic shelf labels (e.g., of the sort detailed below). Briefly, these are electronic displays that can be updated, e.g., by WiFi, Bluetooth or infrared, to present informational displays to shoppers or store personnel. As a robot travels down an aisle and senses products on the shelves, it may interact with one or more of these electronic shelf labels. For example, a robot may—by infrared or wireless command—trigger a shelf label to start flashing, to indicate to a store clerk a stock area that needs replenishment.

Relatedly, as a robot travels an aisle, it can visually examine each of the electronic shelf labels and collect data about its state. If it senses an electronic shelf label indicating $4.39 for a box of Cheerio's cereal, and its database (e.g., table 100) indicates the price for that product at that location should be $4.29, then it can issue an instruction to the electronic unit to change its display to $4.29. (Alternatively or additionally, the robot may note the discrepancy in a report provided to store management.) If the robot finds a shelf label blinking—indicating re-stocking is needed, it can note this too, in a report to store management. (If the blinking was earlier triggered by a robot, the report can indicate how long the blinking has apparently persisted without attention.) In addition to identifying electronic shelf labels that are displaying questionable data, a robot can also identify such labels that are not working.

CONCLUDING REMARKS

Having described and illustrated the principles of our inventive work with reference to illustrative examples, it will be recognized that the technology is not so limited.

For example, while the technology has been described with reference to robot-based image acquisition, the principles are more generally-applicable. For example, store personnel can capture shelf imagery using a mobile phone or a wearable computer, e.g., to do a spot check of planogram compliance. Similarly, drone aircraft can be employed to perform the image acquisition (e.g., as shown in patent document 2014034418).

While the detailed embodiments assumed that each watermarked block on a product's packaging/artwork conveys the same payload, this need not be the case. In some implementations, the blocks convey different payloads. For example, while all blocks may convey the same GTIN identifier, they may additionally convey data indicating the block's position on the package. In one particular embodiment, the blocks are sequentially-numbered, starting from the upper left corner of the printed product/label blank. (Such an arrangement is detailed in applicant's patent publication 20140304122.)

Figure 6:
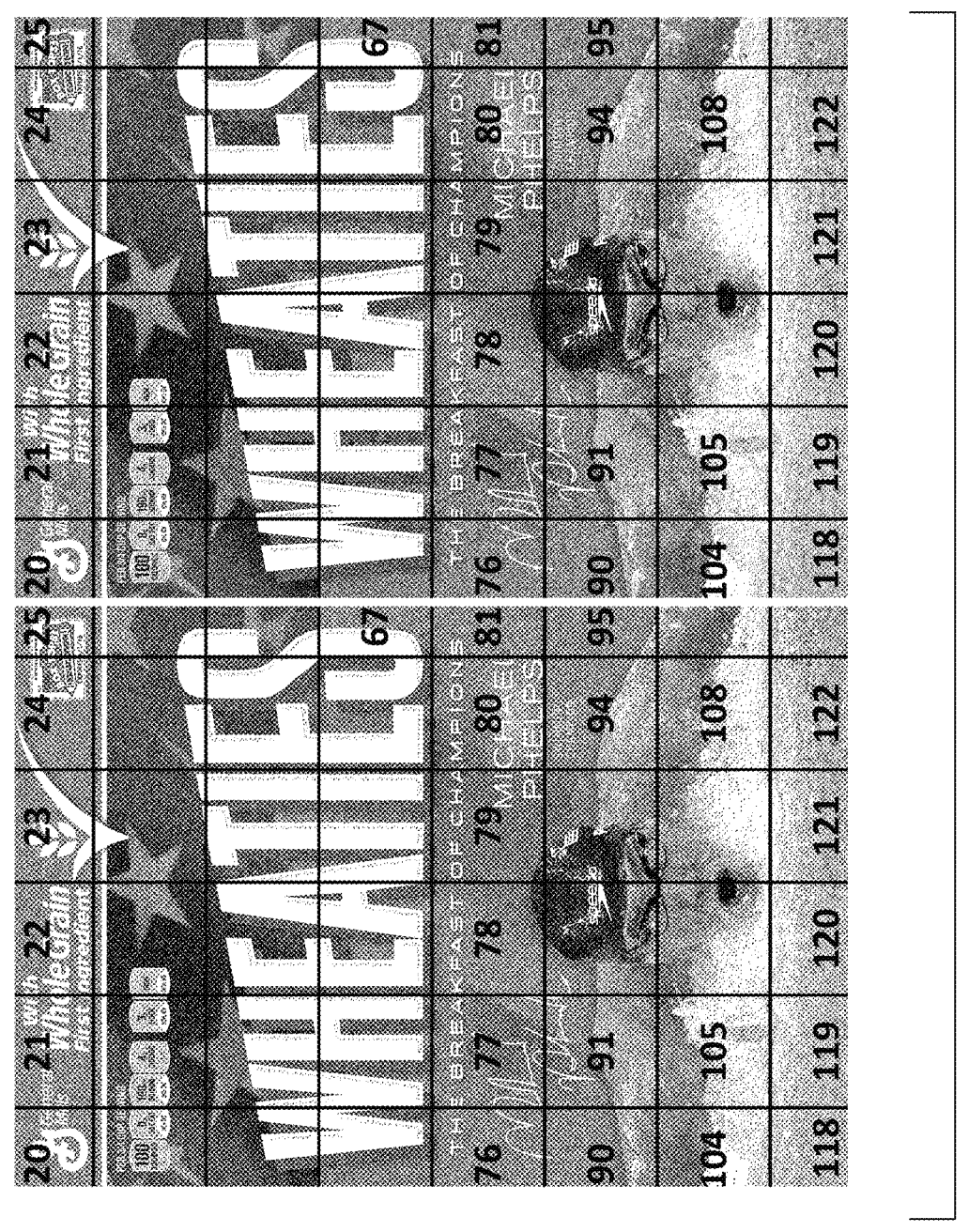

In embodiments in which non-identical block payloads are used, the task of identifying different instances of the same product can be simplified. Consider the arrangement of FIG. 6, in which imagery shows two identical cereal boxes side-by-side. Each watermark payload includes a block serial number. (Not all block serial numbers are shown, for clarity's sake.) The fact that there are two boxes—not just one—can be discerned from the sequencing of block serial numbers. For example, block 20 would never appear to the right of block 25, unless the block 20 was on a different box than block 25. (Ditto, blocks 21, 22, 23 and 24.) Likewise for serial numbers in each row of blocks; the block numbers should always increase to the right. If they decrease, then a different package has been detected.

Similarly, block numbers should increase, moving vertically downward. If this pattern is interrupted—by a decrease in block numbers as moving vertically downward, then this signals detection of a different package.

(The foregoing technique for identifying different instances of identical packages is in addition to the earlier-detailed arrangements, e.g., in which such packages are distinguished by their geometrically inconsistent digital watermark patterns, or by their serialized carton unit number.)

As earlier noted, some embodiments can identify—in captured imagery—the extent of a region watermarked with a certain payload by (after decoding the payload from the watermark) newly generating a watermark pattern from the decoded pattern, and then performing a correlation operation between this newly-generated pattern and other parts of the captured imagery. Within the thus-identified area, the correlation value can serve as a quality metric for the captured imagery. For example, if part of the captured imagery is a bit out of focus, the correlation will suffer in that part, accordingly. (Related approaches are further detailed in patent documents U.S. Pat. No. 7,231,061 (see, e.g., FIG. 2 and related discussion), 20140108020 and in pending application Ser. No. 15/145,784, filed May 3, 2015.)

In other embodiments, location markings can be provided on store shelves. Exemplary markings are watermark or barcode patterns that convey planogram coordinates, e.g., a shelving unit number, a shelf number, and/or a distance from the left edge of the shelving unit.

Such markings can take the form of adhesive labels, applied to the back vertical walls of the shelves. If product is missing from a shelf, a camera viewing the shelf will have a view all the way to the back wall. There the marking is detected, and serves to identify that location within the store's planogram. Detection of the back-wall sticker indicates that inventory for that region of the planogram needs to be re-stocked.

Alternatively, the tops of shelves can be similarly marked, e.g., by a shelf-liner. If the marking is visible, this again indicates that product is missing, and should be re-stocked. Such markings can be sensed by a robot camera that looks vertically downward, e.g., at 45 degrees, as it travels along a shelving unit. If desired, the perspective distortion introduced by this camera view can be corrected-for by application of a corresponding counter-distortion image transformation, before submitting the imagery for decoding.

In still another such arrangement, the undersides of shelves can be so-marked. Such markings can be sensed by a camera that is inclined vertically upward, e.g., at a 45 degree angles, as it travels along a shelving unit. Such arrangement provides planogram location information regardless of whether inventory is stocked on the shelf or not.

In addition to identifying planogram location, such markings can also aid in understanding pose (including scale) of products resting on the shelf. For example, the markings can serve as references by which distances and angles can be discerned.

If such shelf marking is effected by digital watermarking, the watermark pattern can be formed alone (i.e., without host imagery), or it can be encoded within other imagery that serves a marketing purpose (e.g., product advertising), or simply an aesthetic purpose.

Marking arrangements other than adhesive stickers can naturally be used. For example, printing or texturing can be applied directly to the shelving. Alternatively, markings can be projected by ceiling-mounted projectors. Or an electronic shelf-mounted price display can be used. Electronic shelf labels can include a front-facing LCD or other programmable display, a wireless transceiver (for communicating with a remote store computer), and a fastener to mount the label to a front of a shelf. Alternatively, an electronic shelf label may be equipped with a projector that projects such information—such as text and a digital watermark pattern—from the front edge of the shelf towards the wall behind or the shelf above.

In still other embodiments, electronic shelf labels provide planogram location information, e.g., by an index emitted from an RFID chip (which is resolved into shelving unit/shelf/and inches from left edge, using a remote database), or periodically encoded in the electronic shelf label display. In some such embodiments, a camera on the back side of the electronic shelf display looks back, or up, to sense planogram location markings from a back wall of the shelving unit, or from the underside of the shelf above. Such information can then be emitted from the electronic shelf-mounted price display, e.g., by RFID or display.

(Electronic shelf labels are detailed, e.g., in applicant's patent application 20140052555, and in patent documents U.S. Pat. Nos. 7,005,962, 7,213,751, 7,461,782, 20040012485 and 20060100967 assigned to the Swedish company Pricer AB.)

Reference was made to assessing the scale of a watermark block in captured imagery by reference to photogrammetry, as a way of avoiding the need to try watermark detection at multiple scale states.

Another way to shortcut watermark detection is to first obtain a coarse synchronization with the watermark signal. This can be done by processing low resolution imagery to detect spatial frequency impulses that form the watermark's orientation signal. (Such impulses can be detected at resolutions too low to decode the watermark payload itself). From the orientation signal, the presence of a watermark at a particular location (a Region of Interest, or ROI) is known, and information about the pose of the watermarked object at that location can be determined.

If the low-resolution imagery is obtained by down-sampling high resolution imagery, then full-resolution imagery from this area can be submitted to the watermark decoder, counter-distorted to at least roughly counteract affine distortion due to the determined pose. Alternatively, if the original image capture is at low resolution, the ROI data can be used to aim a Pan Tilt Zoom (PTZ) camera to capture high resolution imagery from that location, which again is decoded with some fore-knowledge of the object pose (e.g., permitting counter-distortion).

(The high resolution imagery of the subject is typically sampled at twice—or more—the vertical and horizontal frequency of the low resolution imagery. Thus, if a single inch span of the subject is represented by a line of 50 pixels in the low resolution imagery, that same single inch span would by sampled by 100 or more pixels in the high resolution imagery. Ratios of four-to-one, ten-to-one, or greater, may alternatively be used.)

Alternatively, features of the template recovered at low resolution (or other image features discerned from shelf imagery, e.g., product label SIFT points) are used to estimate the pose of the object using Structure from Motion (SFM) techniques. With this preliminary pose information, a higher resolution image can be processed (or acquired and processed)—again exploiting the fore-knowledge of pose to bound the search space of watermark parameters that must be considered in extracting the payload from the high resolution imagery.

Although certain of the embodiments pre-supposed existence of a store planogram, in other embodiments the present technology can be employed to generate planograms, and to otherwise product-map retail establishments.

The problem of object double-counting (due to depictions of a single object in plural successive image frames) was addressed above, but can also be addressed by predictive analysis of where an object will appear in a subsequent frame, based on a robot's speed down an aisle, and an interval between successive image captures.

By the photogrammetry arrangements noted earlier, the location of an object's depiction in an image frame (e.g., the pixel column number at which the left product edge appears) can be correlated to a physical location on a shelf (e.g., a distance, in inches, from the beginning of the shelf). If the robotic camera platform moves at a speed of six inches per second, and captures an image every 5 seconds, then a given object that appears in two successive image frames will appear to have moved a distance corresponding to 30 inches—as depicted in the camera's field of view. Such knowledge allows the object's latter depiction to be predicted and disregarded in counting inventory. Desirably, digital watermark payload data decoded from the object as depicted in the first frame serves to confirm the identity of the same object as depicted in the second frame.

It will be recognized that the detailed arrangements can also employ beacon technology, e.g., of the sort described in applicant's patent document 20160044460. For example, a beacon can signal location information to a robot, helping direct the robot as to where it should (or should not) go. Indoor positioning can be achieved by reference to beacon signals (e.g., by triangulation techniques).

In some embodiments, the camera-equipped robot, or another mobile robot platform, is equipped with an actuator arm that is used to reposition shelved products so that their placement better conforms to shelf planogram data. In addition to moving items to correct planogram zones, the actuator arm can also be used to re-orient shelved items so that their front faces are oriented parallel to the long axis of the shelf. (This speeds image-based recognition of such items the next time a robotic inspection of the shelf is performed.) The actuator arm may also pull items forward on the shelf, towards the front edge. In some arrangements, a first robot captures and analyzes imagery to identify items having depleted shelf stock, and issue instructions to a second mobile robot to fetch replenishment items from a storeroom, and to shelve them in accordance with store planogram data. Suitable robotic actuators for such tasks are commercially available from multiple vendors, including Fanuc Corporation, Yaskawa Motoman Robotics, Kuka AG, and ABB Ltd. An illustrative actuator is detailed in patent publication 20140363264. An exemplary robotic platform employs the Segway drive system.

While reference has been made, above and elsewhere, to the robot performing various acts, it will be recognized that such acts can be performed by another processor, e.g., a fixed server at the store or remote from the store—either in real time as the robot is performing data collection (and relaying data wirelessly), or later—in an offline process.

While many of the detailed arrangements employed watermarking technologies, image fingerprinting techniques and barcode recognition can be employed in other embodiments. (Fingerprint recognition can be speeded by using different sets of reference fingerprint data, depending on the aisle in which the robot is presently operating. Attempted matching against reference fingerprint data for jars of peanut butter is generally only worthwhile if the robot is in an aisle where peanut butter is stocked.)

The artisan is presumed to be familiar with ancillary image processing techniques, including image segmentation and image stitching. Wikipedia articles for these topics are attached as appendices to priority application 62/164,490 and form part of this disclosure.

It will be recognized that the robotic operations detailed in this specification can be performed outside of normal business hours, and can be performed with the store's usual overhead illumination turned-off, or operating at a greatly-reduced levels (e.g., with illumination on the aisle floors of less than 40—or even 10—footcandles).

The design of servers and other computing devices referenced in this disclosure are familiar to the artisan. In general terms, each includes one or more processors, one or more memories (e.g. RAM), storage (e.g., a disk or flash memory), a user interface (which may include, e.g., a keypad, a TFT LCD or OLED display screen, touch or other gesture sensors, a camera or other optical sensor, one or more microphones, etc., together with software instructions for providing a graphical user interface), interconnections between these elements (e.g., buses), and an interface for communicating with other devices (which may be wireless, such as GSM, 3G, 4G, CDMA, WiFi, WiMax, Zigbee or Bluetooth, and/or wired, such as through an Ethernet local area network, etc The processes and system components detailed in this specification can be implemented as instructions for computing devices, including instructions for a variety of programmable processors, such as microprocessors and systems on a chip (e.g., the Intel Atom, the ARM A8 and Cortex series, the Qualcomm Snapdragon, and the nVidia Tegra 4; the latter includes an ARM CPU, a GPU, and nVidia's Chimera computational photography architecture).

Implementation can also employ a variety of specialized processors, such as graphics processing units (GPUs, such as are included in the nVidia Tegra series, and the Adreno 530—part of the Qualcomm Snapdragon processor), and digital signal processors (e.g., the Texas Instruments TMS320 and OMAP series devices, and the ultra-low power Qualcomm Hexagon devices, such as the QDSP6V5A), etc. These instructions can be implemented as software, firmware, etc. These instructions can also be implemented in various forms of processor circuitry, including programmable logic devices, field programmable gate arrays (e.g., the Xilinx Virtex series devices), field programmable object arrays, and application specific circuits—including digital, analog and mixed analog/digital circuitry. Execution of the instructions can be distributed among processors and/or made parallel across processors within a device or across a network of devices. Processing of data can also be distributed among different processor and memory devices. Cloud computing resources can be used as well. References to "processors," "modules" or "components" should be understood to refer to functionality, rather than requiring a particular form of implementation.

Implementation can additionally, or alternatively, employ special purpose electronic circuitry that has been custom-designed and manufactured to perform some or all of the component acts, as an application specific integrated circuit (ASIC).

To realize such an implementation, the relevant module(s) (e.g., watermark decoding) are first implemented using a general purpose computer, using software such as Matlab (from Mathworks, Inc.). A tool such as HDLCoder (also available from MathWorks) is next employed to convert the MatLab model to VHDL (an IEEE standard, and doubtless the most common hardware design language). The VHDL output is then applied to a hardware synthesis program, such as Design Compiler by Synopsis, HDL Designer by Mentor Graphics, or Encounter RTL Compiler by Cadence Design Systems. The hardware synthesis program provides output data specifying a particular array of electronic logic gates that will realize the technology in hardware form, as a special-purpose machine dedicated to such purpose. This output data is then provided to a semiconductor fabrication contractor, which uses it to produce the customized silicon part. (Suitable contractors include TSMC, Global Foundries, and ON Semiconductors.)

Essentially all of the functions detailed above can be implemented in such fashion, e.g., decoding a watermark payload from captured imagery, querying a planogram database, etc. However, because the resulting circuit is typically not changeable, such implementation is best used for component functions that are unlikely to be revised.

As indicated above, reference to a "module" that performs a certain function should be understood to encompass one or more items of software, and/or one or more hardware circuits—such as an ASIC as just-described.

Software instructions for implementing the detailed functionality can be authored by artisans without undue experimentation from the descriptions provided herein, e.g., written in C, C++, Visual Basic, Java, Python, Tcl, Perl, Scheme, Ruby, etc., in conjunction with associated data.

Software and hardware configuration data/instructions are commonly stored as instructions in one or more data structures conveyed by tangible media, such as magnetic or optical discs, memory cards, ROM, etc., which may be accessed across a network. Some embodiments may be implemented as embedded systems—special purpose computer systems in which operating system software and application software are indistinguishable to the user. Some or all of the functionality detailed in this specification can be implemented in operating system software, application software and/or as embedded system software.

Different of the functionality can be implemented on different devices. For example, in a system in which a computer-based robot gathers imagery, and some of it is processed using a server, based on planogram data from still another computer, different tasks can be performed exclusively by one device or the other, or execution can be distributed between the devices. Extraction of watermark information from imagery is one example of a process that can be distributed in such fashion. Thus, it should be understood that description of an operation as being performed by a particular device (e.g., a server) is not limiting but exemplary; performance of the operation by another device (e.g., a robot or another computer), or shared between devices, is also expressly contemplated.

In like fashion, description of data being stored on a particular device is also exemplary; data can be stored anywhere: local device, remote device, in the cloud, distributed, etc.

As indicated, the present technology can be used in connection with wearable computing systems, including headworn devices. Such devices typically include one or more sensors (e.g., microphone(s), camera(s), accelerometers(s), etc.), and display technology by which computer information can be viewed by the user—either overlaid on the scene in front of the user (sometimes termed augmented reality), or blocking that scene (sometimes termed virtual reality), or simply in the user's peripheral vision. Such an arrangement can present visualizations of the sort shown in FIGS. 3A and 3B, identifying planogram layout and highlighting mis-located products, and gaps in shelf stock.

Details concerning watermarking are known from applicant's previous patent filings, including patent documents U.S. Pat. Nos. 8,401,224, 6,975,744, 6,973,197, 6,912,295, 6,590,996, 6,345,104, 6,307,949, 6,122,403, 20100150434, 20120046071, 20120078989, 20140029809, 20140108020, 20140119593, 20150016664, 20160275639, 20160217547, and 20170024840, and pending application Ser. No. 15/641,081, filed Jul. 3, 2017. Such watermarks are most commonly imperceptible, meaning they are not noticeable to a viewer examining watermarked packaging from a typical viewing distance (e.g., 20 inches) in typical retail lighting (e.g., 50-85 foot-candles), who has not been alerted previously to the existence of such encoding. Spot colors, as are sometimes found on packaging, can be watermarked by leaving tiny voids in the printing to subtly change the luminance or chrominance. Other techniques for watermarking of spot colors are detailed in patent documents U.S. Pat. Nos. 6,763,124, 9,449,357, 20160198064 and 20150156369.

Some of applicant's other work relating to the present technology is detailed in patent documents U.S. Pat. No. 7,340,076, 20140357312, 20140244514, 20140164124, 20120214515, 20120208592, 20020114491, 20150168538, 20140052555, 20160044460 and pending application Ser. No. 15/176,498, filed Jun. 8, 2016.

The following third party patent publications are related to the present subject matter, detailing arrangements in which the present technology can be advantageously employed, and vice versa: WO2016051183, U.S. Pat. Nos. 9,245,160, 9,317,775, 9,330,474, 20100123005, 20140152874, 20140324642, 20140344118, 20150039443, 20150046299, 20150049902, 20150052027, 20150054620, 20150057917, 20150088701, 20150088703, 20150123973, 20150262116, 20150294333, 20150324725, 20150363758, 20150365660, and 20160119540.

Fingerprint-based content identification techniques are also well known. SIFT, SURF, ORB and CONGAS are some of the most popular algorithms. (SIFT, SURF and ORB are each implemented in the popular OpenCV software library, e.g., version 3.) Still other fingerprinting techniques are detailed in patent publications 20090282025, 20060104598, WO2012004626 and WO2012156774 (all by LTU Technologies of France).

Yet other fingerprinting techniques are variously known as Bag of Features, or Bag of Words, methods. Such methods extract local features from patches of an image (e.g., SIFT points), and automatically cluster the features into N groups (e.g., 168 groups)—each corresponding to a prototypical local feature. A vector of occurrence counts of each of the groups (i.e., a histogram) is then determined, and serves as a reference signature for the image. To determine if a query image matches the reference image, local features are again extracted from patches of the image, and assigned to one of the earlier-defined N-groups (e.g., based on a distance measure from the corresponding prototypical local features). A vector occurrence count is again made, and checked for correlation with the reference signature. Further information is detailed, e.g., in Nowak, et al, Sampling strategies for bag-of-features image classification, Computer Vision-ECCV 2006, Springer Berlin Heidelberg, pp. 490-503; and Fei-Fei et al, A Bayesian Hierarchical Model for Learning Natural Scene Categories, IEEE Conference on Computer Vision and Pattern Recognition, 2005; and references cited in such papers.

Optical character recognition (OCR) can be similarly employed to identify objects, and can also be used in embodiments of the present technology.

Convolutional neural network technology for recognizing supermarket items is detailed in pending application Ser. No. 15/726,290, filed Oct. 5, 2017.

This specification has discussed several different embodiments. It should be understood that the methods, elements and concepts detailed in connection with one embodiment can be combined with the methods, elements and concepts detailed in connection with other embodiments. While some such arrangements have been particularly described, many have not—due to the large number of permutations and combinations. Applicant similarly recognizes and intends that the methods, elements and concepts of this specification can be combined, substituted and interchanged—not just among and between themselves, but also with those known from the cited prior art. Moreover, it will be recognized that the detailed technology can be included with other technologies—current and upcoming—to advantageous effect. Implementation of such combinations is straightforward to the artisan from the teachings provided in this disclosure.

While this disclosure has detailed particular ordering of acts and particular combinations of elements, it will be recognized that other contemplated methods may re-order acts (possibly omitting some and adding others), and other contemplated combinations may omit some elements and add others, etc.

Although disclosed as complete systems, sub-combinations of the detailed arrangements are also separately contemplated (e.g., omitting various of the features of a complete system).

While certain aspects of the technology have been described by reference to illustrative methods, it will be recognized that apparatuses configured to perform the acts of such methods are also contemplated as part of applicant's inventive work. Likewise, other aspects have been described by reference to illustrative apparatus, and the methodology performed by such apparatus is likewise within the scope of the present technology. Still further, tangible computer readable media containing instructions for configuring a processor or other programmable system to perform such methods is also expressly contemplated.

To provide a comprehensive disclosure, while complying with the Patent Act's requirement of conciseness, applicant incorporates-by-reference each of the documents referenced herein. (Such materials are incorporated in their entireties, even if cited above in connection with specific of their teachings.) These references disclose technologies and teachings that applicant intends be incorporated into the arrangements detailed herein, and into which the technologies and teachings presently-detailed be incorporated.

The invention claimed is:

1. A method of checking inventory in a retail store, the store including products stocked on shelves positioned adjacent an aisle, the method including the acts:

producing shelf imagery using a robot that navigates along said aisle of said retail store, the robot being equipped with an imaging system comprising one or more cameras and at least one illumination source;

processing a low-resolution counterpart to said shelf imagery to sense presence of machine-readable information at a particular location within the shelf imagery;

based on said particular location, identifying a region of interest containing the machine-readable information; and analyzing a high-resolution counterpart to said region of interest, depicted in said shelf imagery, to decode an identifier from said machine-readable information;

wherein processing of the shelf imagery is reduced due to analysis of said region of interest, rather than all said shelf imagery, to decode said identifier;

the method further including detecting, from said low-resolution counterpart to said shelf imagery, spatial frequency impulses associated with an orientation signal of a digital watermark, said spatial frequency impulses indicating presence of machine-readable digital watermark information.

2. The method of claim 1 that includes stitching together plural image frames captured by said imaging system to produce panoramic imagery, said panoramic imagery serving as said shelf imagery.

3. A method of checking inventory in a retail store, the store including products stocked on shelves positioned adjacent an aisle, the method including the acts:

producing shelf imagery using a robot that navigates along said aisle of said retail store, the robot being equipped with an imaging system comprising one or more cameras and at least one illumination source;

processing a low-resolution counterpart to said shelf imagery to sense presence of machine-readable information at a particular location within the shelf imagery;

based on said particular location, identifying a region of interest containing the machine-readable information; and analyzing a high-resolution counterpart to said region of interest, depicted in said shelf imagery, to decode an identifier from said machine-readable information;

wherein processing of the shelf imagery is reduced due to analysis of said region of interest, rather than all said shelf imagery, to decode said identifier; and the machine-readable information is sensed from an electronic shelf label.

4. The method of claim 3 that further includes the robot emitting a signal causing the electronic shelf label to change its display.

5. A method of checking inventory in a retail store, the store including products stocked on shelves positioned adjacent an aisle, the method including the acts:

producing shelf imagery using a robot that navigates along said aisle of said retail store, the robot being equipped with an imaging system comprising one or more cameras and at least one illumination source;

processing a low-resolution counterpart to said shelf imagery to sense presence of machine-readable information at a particular location within the shelf imagery;

based on said particular location, identifying a region of interest containing the machine-readable information; and analyzing a high-resolution counterpart to said region of interest, depicted in said shelf imagery, to decode an identifier from said machine-readable information;

wherein processing of the shelf imagery is reduced due to analysis of said region of interest, rather than all said shelf imagery, to decode said identifier;

the method further including varying illumination emitted by said illumination source as the robot navigates along the aisle.

6. The method of claim 5 in which said varying is triggered by image data collected by said imaging system.

7. A method of checking inventory in a retail store, the store including products stocked on shelves positioned adjacent an aisle, the method including the acts:

producing shelf imagery using a robot that navigates along said aisle of said retail store, the robot being equipped with an imaging system comprising one or more cameras and at least one illumination source;

processing a low-resolution counterpart to said shelf imagery to sense presence of machine-readable information at a particular location within the shelf imagery;

based on said particular location, identifying a region of interest containing the machine-readable information; and analyzing a high-resolution counterpart to said region of interest, depicted in said shelf imagery, to decode an identifier from said machine-readable information;

wherein processing of the shelf imagery is reduced due to analysis of said region of interest, rather than all said shelf imagery, to decode said identifier;

the method further including varying a spectrum of illumination emitted by said illumination source as the robot navigates along the aisle.

8. A method of checking inventory in a retail store, the store including products stocked on shelves positioned adjacent an aisle, the method including the acts:

producing shelf imagery using a robot that navigates along said aisle of said retail store, the robot being equipped with an imaging system comprising one or more cameras and at least one illumination source;

processing a low-resolution counterpart to said shelf imagery to sense presence of machine-readable information at a particular location within the shelf imagery;

based on said particular location, identifying a region of interest containing the machine-readable information; and analyzing a high-resolution counterpart to said region of interest, depicted in said shelf imagery, to decode an identifier from said machine-readable information;

wherein processing of the shelf imagery is reduced due to analysis of said region of interest, rather than all said shelf imagery, to decode said identifier; and said decoded identifier indicates a first product that should be stocked in an adjoining product region, the method further including:

consulting a data structure to determine a width of said product region for the indicated first product;

by reference to information including a position of the detected shelf label in the shelf imagery, and said determined width of the product region, identifying an excerpt of the shelf imagery within which the first product should be depicted; and identifying one or more instances of product items depicted within said identified excerpt.

9. The method of claim 8 that includes identifying an instance of a product item within said identified excerpt that is different than said first product, and reporting same as an exception.

10. The method of claim 8 in which the machine-readable information is presented on a medium having a known width, and the method includes using said known width as a measuring reference in identifying said excerpt of the shelf imagery within which the first product should be depicted.

11. The method of claim 10 that includes determining, from the shelf imagery, a number of pixels per inch for depiction of said medium of known width, and using said determined number to establish a width of said excerpt, in pixels.

12. The method of claim 10 that includes determining, from the shelf imagery, a pixel-width of said medium, and multiplying said pixel-width by a ratio between the width of the product region and the width of the medium to determine a pixel-width of the product region.

13. The method of claim 10 that includes using a known width of the medium to limit a search space for recognizing instances of product items depicted within said identified excerpt, since a range of possible scales at which said items may be depicted within said excerpt can thereby be estimated.

14. The method of claim 10 that includes identifying fewer instances of the first product within said product region than expected, and reporting same as an exception.

15. The method of claim 10 in which the camera system includes one camera oriented to view towards the horizon, and a second camera oriented to view above the horizon, wherein the shelf imagery is produced using image data collected by the second camera, and the method includes processing said image data collected by the second camera to compensate for perspective distortion resulting from said view above the horizon.

16. The method of claim 1 in which the machine-readable information is sensed from an electronic shelf label.

17. The method of claim 1 that includes varying illumination emitted by said illumination source as the robot navigates along the aisle.

18. The method of claim 1 that includes varying a spectrum of illumination emitted by said illumination source as the robot navigates along the aisle.

19. The method of claim 1 in which said decoded identifier indicates a first product that should be stocked in an adjoining product region, and the method further includes:
consulting a data structure to determine a width of said product region for the indicated first product;
by reference to information including a position of the detected shelf label in the shelf imagery, and said determined width of the product region, identifying an excerpt of the shelf imagery within which the first product should be depicted; and
identifying one or more instances of product items depicted within said identified excerpt.

20. The method of claim 3 that further includes varying illumination emitted by said illumination source as the robot navigates along the aisle.

21. The method of claim 3 that further includes varying a spectrum of illumination emitted by said illumination source as the robot navigates along the aisle.

22. The method of claim 3 in which said decoded identifier indicates a first product that should be stocked in an adjoining product region, and the method further includes:
consulting a data structure to determine a width of said product region for the indicated first product;
by reference to information including a position of the detected shelf label in the shelf imagery, and said determined width of the product region, identifying an excerpt of the shelf imagery within which the first product should be depicted; and
identifying one or more instances of product items depicted within said identified excerpt.

23. The method of claim 5 that further includes varying a spectrum of illumination emitted by said illumination source as the robot navigates along the aisle.

24. The method of claim 5 in which said decoded identifier indicates a first product that should be stocked in an adjoining product region, and the method further includes:
consulting a data structure to determine a width of said product region for the indicated first product;
by reference to information including a position of the detected shelf label in the shelf imagery, and said determined width of the product region, identifying an excerpt of the shelf imagery within which the first product should be depicted; and
identifying one or more instances of product items depicted within said identified excerpt.

25. The method of claim 7 in which said decoded identifier indicates a first product that should be stocked in an adjoining product region, and the method further includes:
consulting a data structure to determine a width of said product region for the indicated first product;
by reference to information including a position of the detected shelf label in the shelf imagery, and said determined width of the product region, identifying an excerpt of the shelf imagery within which the first product should be depicted; and
identifying one or more instances of product items depicted within said identified excerpt.

* * * * *